US010595762B2

(12) United States Patent
Ivosevic et al.

(10) Patent No.: US 10,595,762 B2
(45) Date of Patent: Mar. 24, 2020

(54) BLOOD SAMPLE MANAGEMENT USING OPEN CELL FOAM

(71) Applicant: Becton, Dickinson and Company, Franklin Lakes, NJ (US)

(72) Inventors: Milan Ivosevic, Kinnelon, NJ (US); Bradley M. Wilkinson, North Haledon, NJ (US); C. Mark Newby, Tuxedo, NY (US); Kishore K. Bokka Srinivasa Rao, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/097,725

(22) Filed: Apr. 13, 2016

(65) Prior Publication Data

US 2016/0220160 A1    Aug. 4, 2016

Related U.S. Application Data

(62) Division of application No. 14/861,136, filed on Sep. 22, 2015, now Pat. No. 9,693,723.

(Continued)

(51) Int. Cl.
*A61B 5/15* (2006.01)
*A61J 1/14* (2006.01)
(Continued)

(52) U.S. Cl.
CPC ........ *A61B 5/150755* (2013.01); *A61B 5/151* (2013.01); *A61B 5/150022* (2013.01);
(Continued)

(58) Field of Classification Search
CPC ....... A61J 1/1412; A61J 1/1475; B01L 3/502; B01L 3/502707; B01L 3/502746; B01L 3/567; G01N 1/36
(Continued)

(56) References Cited

U.S. PATENT DOCUMENTS 3,626,929 A    12/1971   Sanz
3,819,913 A     6/1974   Carter et al.
(Continued)

FOREIGN PATENT DOCUMENTS

CN    101036591 A    9/2007
CN    102119017 A    7/2011
(Continued)

*Primary Examiner* — Jill A Warden
*Assistant Examiner* — Jacqueline Brazin
(74) *Attorney, Agent, or Firm* — The Webb Law Firm

(57) ABSTRACT

A specimen transfer device adapted to receive a blood sample is disclosed. The specimen transfer device includes a housing and an actuation member. A deformable material is disposed within the housing and is deformable from an initial position in which the material is adapted to hold the sample to a deformed position in which at least a portion of the sample is released from the material. A viscoelastic member is disposed within the housing between the material and the housing and between the material and the actuation member. The viscoelastic member is engaged with the actuation member and the material such that movement of the actuation member from a first position to a second position deforms the material from the initial position to the deformed position.

14 Claims, 23 Drawing Sheets

Related U.S. Application Data

(60) Provisional application No. 62/063,536, filed on Oct. 14, 2014, provisional application No. 62/207,618, filed on Aug. 20, 2015.

(51) Int. Cl.

| | | |
|---|---|---|
| *A61B 5/151* | (2006.01) | |
| *A61J 1/06* | (2006.01) | |
| *B01L 3/00* | (2006.01) | |
| *G01N 1/36* | (2006.01) | |
| *A61B 10/00* | (2006.01) | |

(52) U.S. Cl.
CPC ...... *A61B 5/15113* (2013.01); *A61B 5/15142* (2013.01); *A61B 5/150221* (2013.01); *A61B 5/150236* (2013.01); *A61B 5/150244* (2013.01); *A61B 5/150259* (2013.01); *A61B 5/150305* (2013.01); *A61B 5/150343* (2013.01); *A61B 5/150351* (2013.01); *A61B 5/150366* (2013.01); *A61J 1/067* (2013.01); *A61J 1/1412* (2013.01); *A61J 1/1475* (2013.01); *B01L 3/502* (2013.01); *B01L 3/502707* (2013.01); *B01L 3/502746* (2013.01); *B01L 3/567* (2013.01); *G01N 1/36* (2013.01); *A61B 10/0045* (2013.01); *B01L 2200/12* (2013.01); *B01L 2300/042* (2013.01); *B01L 2300/069* (2013.01); *B01L 2300/0838* (2013.01); *B01L 2300/0858* (2013.01); *B01L 2300/12* (2013.01); *B01L 2300/123* (2013.01); *B01L 2300/16* (2013.01); *B01L 2400/0478* (2013.01); *B01L 2400/06* (2013.01); *B01L 2400/08* (2013.01); *B01L 2400/086* (2013.01); *B01L 2400/088* (2013.01)

(58) Field of Classification Search
USPC ...................................................... 422/501
See application file for complete search history.

(56) References Cited

U.S. PATENT DOCUMENTS

| | | |
|---|---|---|
| 3,916,205 A | 10/1975 | Kleinerman |
| 3,963,350 A | 6/1976 | Watanabe et al. |
| 4,088,448 A | 5/1978 | Lilja et al. |
| 4,125,828 A | 11/1978 | Resnick et al. |
| 4,133,304 A | 1/1979 | Bailey |
| 4,133,873 A | 1/1979 | Noller |
| 4,337,222 A | 6/1982 | Kitajima et al. |
| 4,501,496 A | 2/1985 | Griffin |
| 4,703,761 A | 11/1987 | Rathbone et al. |
| 4,727,020 A | 2/1988 | Recktenwald |
| 4,751,188 A | 6/1988 | Valet |
| 4,857,735 A | 8/1989 | Noller |
| 4,959,305 A | 9/1990 | Woodrum |
| 5,014,718 A | 5/1991 | Mitchen |
| 5,053,626 A | 10/1991 | Tillotson |
| 5,073,857 A | 12/1991 | Peters et al. |
| 5,102,625 A | 4/1992 | Milo |
| 5,134,662 A | 7/1992 | Bacus et al. |
| 5,159,642 A | 10/1992 | Kosaka |
| 5,187,749 A | 2/1993 | Sugimoto et al. |
| 5,196,709 A | 3/1993 | Berndt et al. |
| 5,200,152 A | 4/1993 | Brown |
| 5,294,799 A | 3/1994 | Aslund et al. |
| 5,332,905 A | 7/1994 | Brooker et al. |
| 5,348,859 A | 9/1994 | Brunhouse et al. |
| 5,385,539 A | 1/1995 | Maynard |
| 5,489,771 A | 2/1996 | Beach et al. |
| 5,491,343 A | 2/1996 | Brooker |
| 5,528,045 A | 6/1996 | Hoffman et al. |
| 5,547,849 A | 8/1996 | Baer et al. |
| 5,556,764 A | 9/1996 | Sizto et al. |
| 5,592,291 A | 1/1997 | Iida |
| 5,599,668 A | 2/1997 | Stimpson et al. |
| 5,627,037 A | 5/1997 | Ward et al. |
| 5,661,558 A | 8/1997 | Nogami et al. |
| 5,674,457 A | 10/1997 | Williamsson et al. |
| 5,675,155 A | 10/1997 | Pentoney, Jr. et al. |
| 5,681,529 A | 10/1997 | Taguchi et al. |
| 5,692,503 A | 12/1997 | Kuenstner |
| 5,732,150 A | 3/1998 | Zhou et al. |
| 5,733,721 A | 3/1998 | Hemstreet, III et al. |
| 5,770,158 A * | 6/1998 | Eischen ................. B01L 3/022 422/520 |
| 5,773,301 A | 6/1998 | Ziegler |
| 5,851,835 A | 12/1998 | Groner |
| 5,890,828 A | 4/1999 | Gueret |
| 5,898,487 A | 4/1999 | Hage |
| 5,933,233 A | 8/1999 | Günther |
| 5,938,439 A | 8/1999 | Mertins et al. |
| 6,043,880 A | 3/2000 | Andrews et al. |
| 6,064,474 A | 5/2000 | Lee et al. |
| 6,064,897 A | 5/2000 | Lindberg et al. |
| 6,094,592 A | 7/2000 | Yorkey et al. |
| 6,103,197 A | 8/2000 | Werner |
| 6,154,282 A | 11/2000 | Lilge et al. |
| 6,159,740 A | 12/2000 | Hudson et al. |
| 6,181,418 B1 | 1/2001 | Palumbo et al. |
| 6,187,592 B1 | 2/2001 | Gourley |
| 6,214,629 B1 | 4/2001 | Freitag et al. |
| 6,226,347 B1 | 5/2001 | Golenhofen |
| 6,262,798 B1 | 7/2001 | Shepherd et al. |
| 6,294,094 B1 | 9/2001 | Muller et al. |
| 6,305,804 B1 | 10/2001 | Rice et al. |
| 6,342,376 B1 | 1/2002 | Kozian et al. |
| 6,350,613 B1 | 2/2002 | Wardlaw et al. |
| 6,410,341 B1 | 6/2002 | Freitag et al. |
| 6,448,018 B1 | 9/2002 | Nakayama et al. |
| 6,453,060 B1 | 9/2002 | Riley et al. |
| 6,477,394 B2 | 11/2002 | Rice et al. |
| 6,479,299 B1 | 11/2002 | Parce et al. |
| 6,493,567 B1 | 12/2002 | Krivitski et al. |
| 6,519,025 B2 | 2/2003 | Shepherd et al. |
| 6,563,585 B1 | 5/2003 | Rao et al. |
| 6,594,075 B1 | 7/2003 | Kanao et al. |
| 6,611,320 B1 | 8/2003 | Lindberg et al. |
| 6,612,111 B1 | 9/2003 | Hodges et al. |
| 6,638,769 B2 | 10/2003 | Lilja et al. |
| 6,665,060 B1 | 12/2003 | Zahniser et al. |
| 6,696,240 B1 | 2/2004 | Kloepfer et al. |
| 6,716,588 B2 | 4/2004 | Sammak et al. |
| 6,723,290 B1 | 4/2004 | Wardlaw |
| 6,740,527 B1 | 5/2004 | Wong et al. |
| 6,825,921 B1 | 11/2004 | Modlin et al. |
| 6,828,567 B2 | 12/2004 | Amirkhanian et al. |
| 6,831,733 B2 | 12/2004 | Pettersson et al. |
| 6,858,400 B2 | 2/2005 | Bristow |
| 6,862,534 B2 | 3/2005 | Sterling et al. |
| 6,869,405 B2 | 3/2005 | Marsden |
| 6,869,570 B2 | 3/2005 | Wardlaw |
| 6,898,458 B2 | 5/2005 | Zeng et al. |
| 6,960,165 B2 | 11/2005 | Ueno et al. |
| 6,985,224 B2 | 1/2006 | Hart |
| 6,999,173 B2 | 2/2006 | Kleinfeld et al. |
| 7,075,628 B2 | 7/2006 | Shepherd et al. |
| 7,094,562 B2 | 8/2006 | Bittner |
| 7,096,124 B2 | 8/2006 | Sterling et al. |
| 7,115,841 B2 | 10/2006 | Zeng et al. |
| 7,133,545 B2 | 11/2006 | Douglass et al. |
| 7,139,073 B1 | 11/2006 | Terada |
| 7,146,372 B2 | 12/2006 | Bacus et al. |
| 7,149,332 B2 | 12/2006 | Bacus et al. |
| 7,271,912 B2 | 9/2007 | Sterling et al. |
| 7,279,134 B2 | 10/2007 | Chan et al. |
| 7,303,922 B2 | 12/2007 | Jeng et al. |
| 7,319,894 B2 | 1/2008 | Higgins |
| 7,324,674 B2 | 1/2008 | Ozawa et al. |
| 7,378,054 B2 | 5/2008 | Karmali |
| 7,420,660 B2 | 9/2008 | Muller |
| 7,426,407 B2 | 9/2008 | Higgins |
| 7,477,382 B2 | 1/2009 | Grey et al. |

(56) References Cited

U.S. PATENT DOCUMENTS

| | | |
|---|---|---|
| 7,500,569 B2 | 3/2009 | Manoussakis et al. |
| 7,515,268 B1 | 4/2009 | Ayliffe et al. |
| 7,518,727 B2 | 4/2009 | Pentoney, Jr. et al. |
| 7,539,335 B2 | 5/2009 | Fukuyama |
| 7,560,073 B1 | 7/2009 | Peters et al. |
| 7,625,712 B2 | 12/2009 | Paul et al. |
| 7,630,063 B2 | 12/2009 | Padmanabhan et al. |
| 7,674,598 B2 | 3/2010 | Paul et al. |
| 7,738,094 B2 | 6/2010 | Goldberg |
| 7,762,946 B2 | 7/2010 | Sugimoto |
| 7,781,226 B2 | 8/2010 | McDevitt et al. |
| 7,790,464 B2 | 9/2010 | Tarasev |
| 7,816,135 B2 | 10/2010 | Goldberg |
| 7,826,728 B2 | 11/2010 | Konno et al. |
| 7,854,891 B2 | 12/2010 | Yamamoto et al. |
| 7,892,551 B2 | 2/2011 | Glencross |
| 7,903,241 B2 | 3/2011 | Wardlaw et al. |
| 7,952,692 B2 | 5/2011 | Primack et al. |
| 8,009,894 B2 | 8/2011 | Lindberg et al. |
| 8,125,623 B2 | 2/2012 | Munger et al. |
| 8,224,058 B2 | 7/2012 | Lindberg et al. |
| 8,244,021 B2 | 8/2012 | Lett et al. |
| 8,306,594 B2 | 11/2012 | Paseman et al. |
| 8,353,848 B2 | 1/2013 | Long et al. |
| 8,377,398 B2 | 2/2013 | McDevitt et al. |
| 8,406,859 B2 | 3/2013 | Zuzak et al. |
| 8,483,789 B2 | 7/2013 | Higgins |
| 8,488,903 B2 | 7/2013 | Higuchi |
| 8,541,227 B2 | 9/2013 | Christensen et al. |
| 8,630,016 B2 | 1/2014 | Swenson et al. |
| 9,693,723 B2 | 7/2017 | Ivosevic et al. |
| 2002/0143298 A1 | 10/2002 | Marsden |
| 2002/0164825 A1* | 11/2002 | Chen ............... G01N 33/56966 436/526 |
| 2003/0123047 A1 | 7/2003 | Pettersson et al. |
| 2003/0152927 A1 | 8/2003 | Jakobsen et al. |
| 2003/0170613 A1 | 9/2003 | Straus |
| 2003/0206828 A1 | 11/2003 | Bell |
| 2003/0230728 A1 | 12/2003 | Dai et al. |
| 2004/0224329 A1 | 11/2004 | Gjerde et al. |
| 2005/0054949 A1 | 3/2005 | McKinnon et al. |
| 2005/0139547 A1 | 6/2005 | Manoussakis et al. |
| 2005/0142565 A1 | 6/2005 | Samper et al. |
| 2005/0190058 A1 | 9/2005 | Call |
| 2005/0232813 A1 | 10/2005 | Karmali |
| 2006/0020531 A1 | 1/2006 | Veeneman et al. |
| 2006/0024756 A1 | 2/2006 | Tibbe et al. |
| 2006/0060531 A1 | 3/2006 | Coville et al. |
| 2006/0241495 A1 | 10/2006 | Kurtz |
| 2006/0252079 A1 | 11/2006 | Oldham et al. |
| 2007/0132994 A1 | 6/2007 | Kobayashi et al. |
| 2007/0178009 A1 | 8/2007 | Sakaino et al. |
| 2008/0190220 A1 | 8/2008 | Backes et al. |
| 2008/0203319 A1 | 8/2008 | Pentoney et al. |
| 2008/0268469 A1 | 10/2008 | Srienc et al. |
| 2009/0024060 A1 | 1/2009 | Darrigrand et al. |
| 2009/0075324 A1 | 3/2009 | Pettersson |
| 2009/0107903 A1 | 4/2009 | Dassa |
| 2009/0130646 A1 | 5/2009 | Fletcher et al. |
| 2009/0173685 A1 | 7/2009 | Imai et al. |
| 2009/0181411 A1 | 7/2009 | Battrell et al. |
| 2009/0259145 A1 | 10/2009 | Bartleld et al. |
| 2010/0285520 A1 | 11/2010 | Halverson et al. |
| 2010/0291599 A1 | 11/2010 | Tague, Jr. et al. |
| 2010/0314461 A1 | 12/2010 | Gruenbacher et al. |
| 2011/0106046 A1 | 5/2011 | Hiranuma et al. |
| 2011/0118139 A1 | 5/2011 | Mehta et al. |
| 2011/0159457 A1* | 6/2011 | Offermann ............. A61B 5/417 433/91 |
| 2011/0159533 A1 | 6/2011 | Karkouche |
| 2012/0016265 A1 | 1/2012 | Peterson et al. |
| 2012/0016307 A1 | 1/2012 | Burkholz et al. |
| 2012/0123297 A1 | 5/2012 | Brancazio |
| 2013/0045529 A1 | 2/2013 | Goldberg et al. |
| 2013/0076019 A1 | 3/2013 | Takemoto |
| 2013/0162990 A1 | 6/2013 | Kobayashi et al. |
| 2014/0073990 A1 | 3/2014 | Holmes et al. |
| 2014/0093896 A1* | 4/2014 | Mongale ............. G01N 33/523 435/19 |
| 2014/0176939 A1 | 6/2014 | Shah et al. |
| 2014/0200154 A1 | 7/2014 | Sugarman et al. |
| 2014/0269160 A1 | 9/2014 | Chee Mun |
| 2015/0125882 A1 | 5/2015 | Bornheimer et al. |
| 2015/0125883 A1 | 5/2015 | Gordon et al. |
| 2015/0132789 A1 | 5/2015 | Bornheimer et al. |
| 2016/0100783 A1 | 4/2016 | Ivosevic et al. |

FOREIGN PATENT DOCUMENTS

| | | |
|---|---|---|
| CN | 202141619 U | 2/2012 |
| CN | 103068307 A | 4/2013 |
| CN | 202928839 U | 5/2013 |
| CN | 03785945 U | 8/2014 |
| CN | 205181357 U | 4/2016 |
| CN | 205317561 U | 6/2016 |
| EP | 0545500 A1 | 6/1993 |
| EP | 0545500 A1 | 9/1993 |
| EP | 0663070 B1 | 7/1995 |
| EP | 0681177 A1 | 11/1995 |
| EP | 0681177 B1 | 11/1995 |
| EP | 0737855 A1 | 10/1996 |
| EP | 0744600 A1 | 11/1996 |
| EP | 0744600 B1 | 11/1996 |
| EP | 0788615 A1 | 8/1997 |
| EP | 0788615 B1 | 8/1997 |
| EP | 0800074 A1 | 10/1997 |
| EP | 0800074 B1 | 10/1997 |
| EP | 0809807 B1 | 12/1997 |
| EP | 0818682 A2 | 1/1998 |
| EP | 0818682 B1 | 1/1998 |
| EP | 0821784 B1 | 2/1998 |
| EP | 0959346 A2 | 11/1999 |
| EP | 0969279 A2 | 1/2000 |
| EP | 0969279 B1 | 1/2000 |
| EP | 1324021 A1 | 7/2003 |
| EP | 1324021 B1 | 7/2003 |
| EP | 1347702 A2 | 10/2003 |
| EP | 1405073 B1 | 4/2004 |
| EP | 1456649 B1 | 9/2004 |
| EP | 1558934 B1 | 8/2005 |
| EP | 1698883 A1 | 9/2006 |
| EP | 1698883 B1 | 9/2006 |
| EP | 1701150 A1 | 9/2006 |
| EP | 1813349 A1 | 1/2007 |
| EP | 1767935 A1 | 3/2007 |
| EP | 1924195 A2 | 5/2008 |
| EP | 2298407 A1 | 5/2008 |
| EP | 1990638 A1 | 11/2008 |
| EP | 2016390 A1 | 1/2009 |
| EP | 2016390 B1 | 1/2009 |
| EP | 2041549 A1 | 4/2009 |
| EP | 2083687 A1 | 8/2009 |
| EP | 2232442 A1 | 9/2010 |
| EP | 2586370 A2 | 5/2013 |
| EP | 2605020 A2 | 6/2013 |
| EP | 2676606 A1 | 12/2013 |
| JP | 62181056 A | 8/1987 |
| JP | 10323341 A | 12/1998 |
| JP | 11318871 A | 11/1999 |
| JP | 200074906 A | 3/2000 |
| JP | 2000176006 A | 6/2000 |
| JP | 2000262271 A | 9/2000 |
| JP | 200188098 A | 4/2001 |
| JP | 2001324500 A | 11/2001 |
| JP | 2002506208 A | 2/2002 |
| JP | 2002516982 A | 6/2002 |
| JP | 200319126 A | 1/2003 |
| JP | 20056821 A | 1/2005 |
| JP | 200517280 A | 1/2005 |
| JP | 200517281 A | 1/2005 |
| JP | 2007518978 A | 7/2007 |
| JP | 2008525768 A | 7/2008 |
| JP | 4255556 B2 | 4/2009 |
| JP | 2009525819 A | 7/2009 |

(56) References Cited

FOREIGN PATENT DOCUMENTS

| | | | |
|---|---|---|---|
| JP | 201195157 | A | 5/2011 |
| JP | 2011133235 | A | 7/2011 |
| JP | 2011529573 | A | 12/2011 |
| JP | 2012137493 | A | 7/2012 |
| JP | 201396797 | A | 5/2013 |
| NL | 6909366 | A | 1/1970 |
| WO | 9920998 | A1 | 4/1999 |
| WO | 9945384 | A1 | 9/1999 |
| WO | 0028297 | A2 | 5/2000 |
| WO | 0029847 | A2 | 5/2000 |
| WO | 0244729 | A1 | 6/2002 |
| WO | 0250518 | A2 | 6/2002 |
| WO | 03036290 | A1 | 5/2003 |
| WO | 2004100887 | A2 | 11/2004 |
| WO | 2005100539 | A2 | 10/2005 |
| WO | 2006047831 | A1 | 5/2006 |
| WO | 2006096126 | A1 | 9/2006 |
| WO | 2006119368 | A2 | 11/2006 |
| WO | 2006124756 | A2 | 11/2006 |
| WO | 2007012975 | A1 | 2/2007 |
| WO | 2007033318 | A2 | 3/2007 |
| WO | 2007051861 | A1 | 5/2007 |
| WO | 2007111555 | A1 | 10/2007 |
| WO | 2007129948 | A1 | 11/2007 |
| WO | 2007145328 | A1 | 12/2007 |
| WO | 2008002462 | A2 | 1/2008 |
| WO | 2008010761 | A1 | 1/2008 |
| WO | 2008037068 | A1 | 4/2008 |
| WO | 2008103992 | A2 | 8/2008 |
| WO | 2009091318 | A1 | 7/2009 |
| WO | 2009155612 | A2 | 12/2009 |
| WO | WO20090155612 | A2 | 12/2009 |
| WO | 2010003518 | A1 | 1/2010 |
| WO | 2010085658 | A1 | 7/2010 |
| WO | 2011133540 | A2 | 10/2011 |
| WO | 2012117648 | A1 | 9/2012 |
| WO | 2013075031 | A1 | 5/2013 |
| WO | 2013128177 | A1 | 9/2013 |
| WO | WO 2013128177 | * | 9/2013 |

* cited by examiner

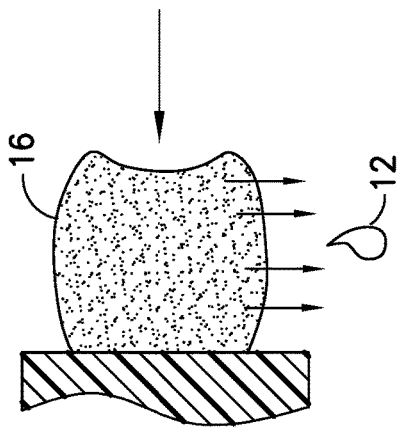
FIG.1C
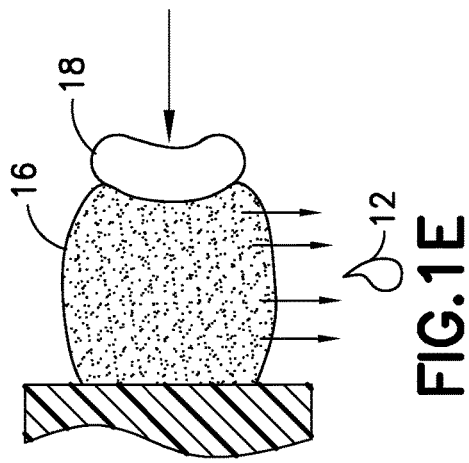
FIG.1E
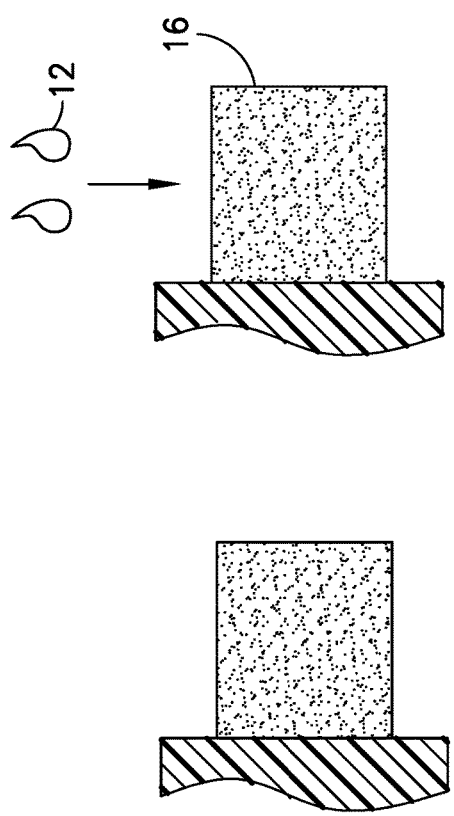
FIG.1A
FIG.1B
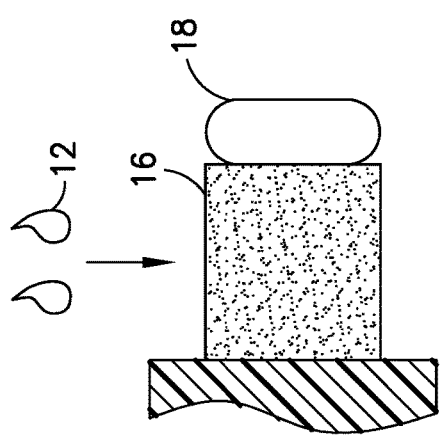
FIG.1D

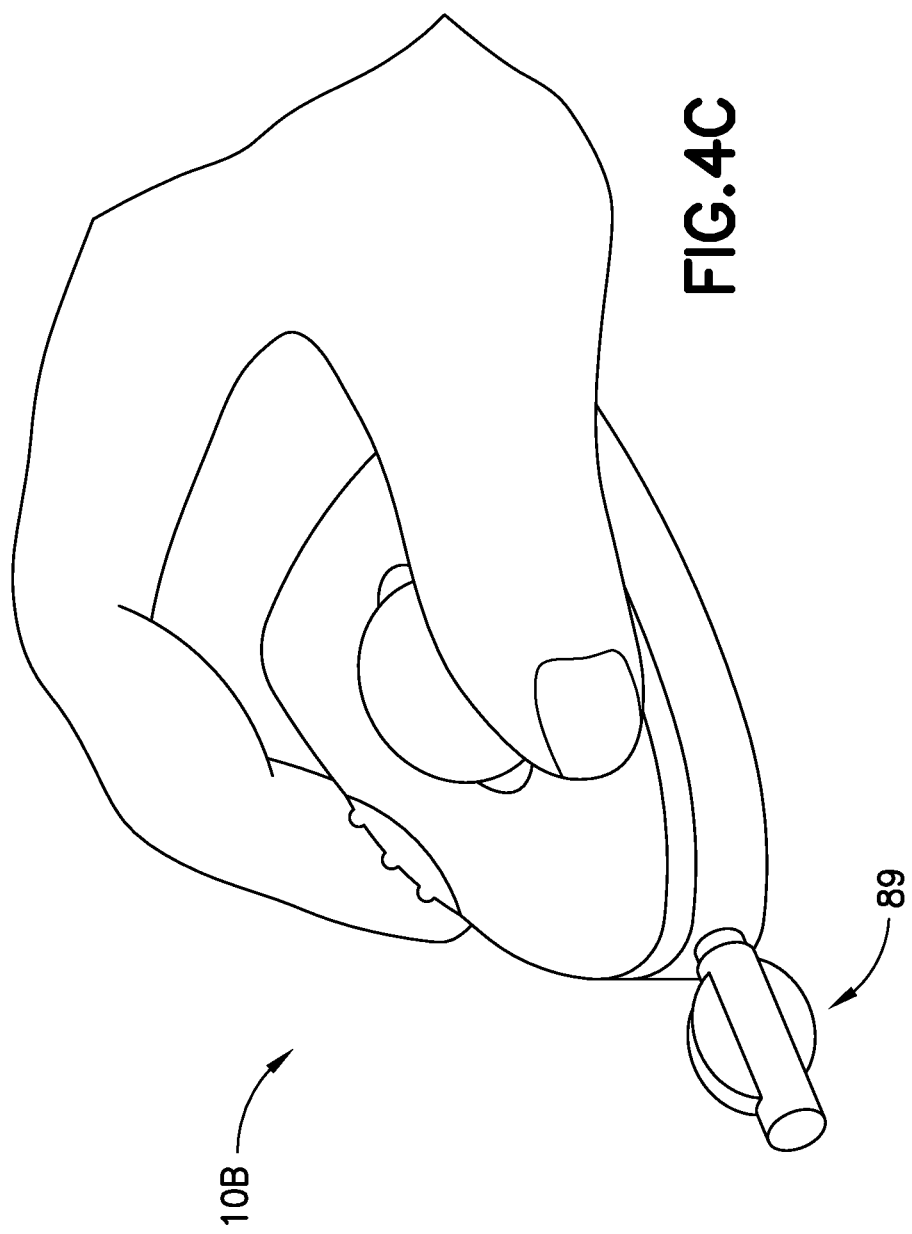

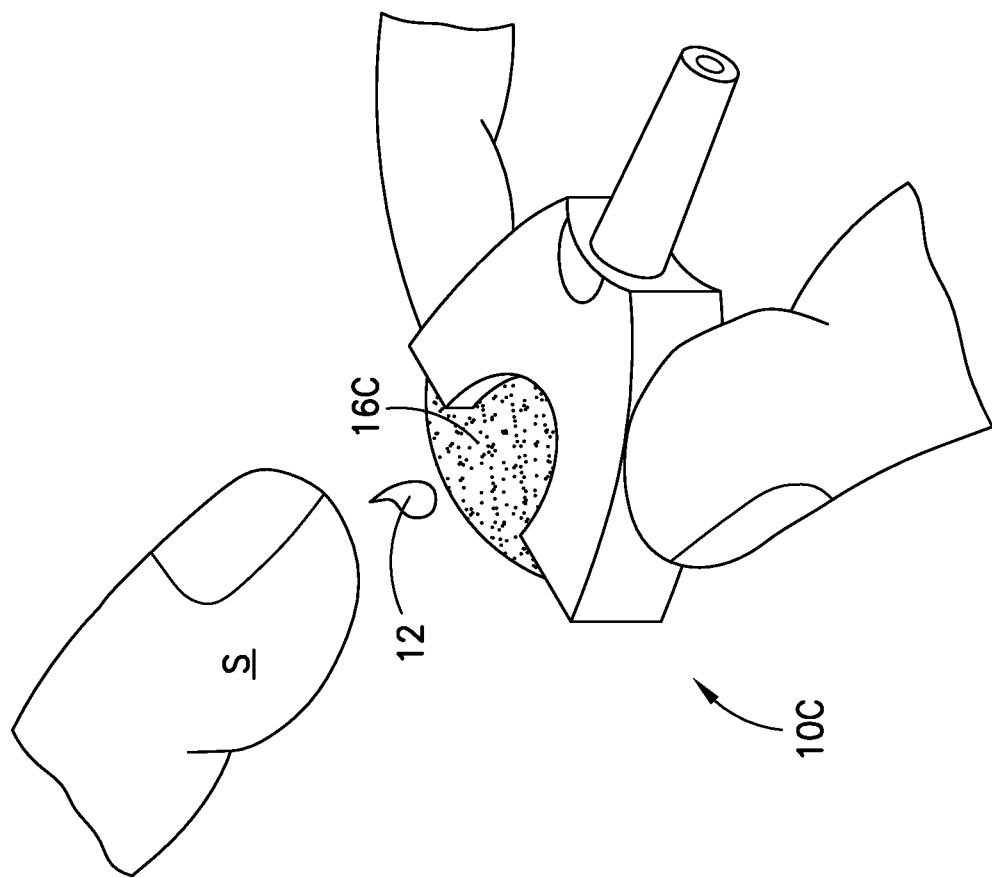
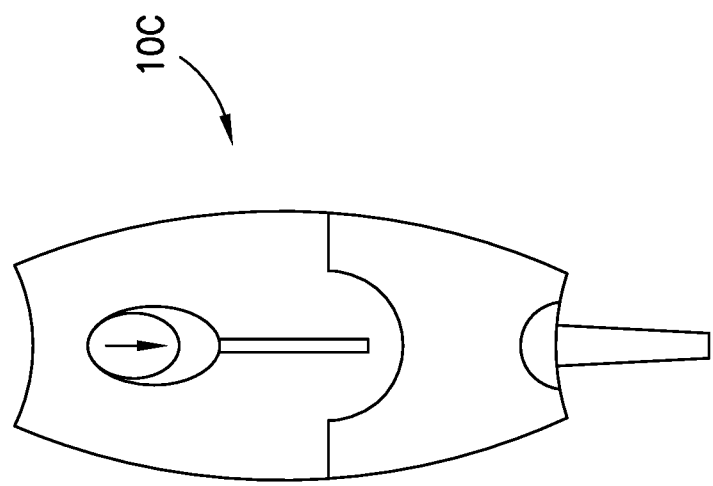
FIG.5B
FIG.5A

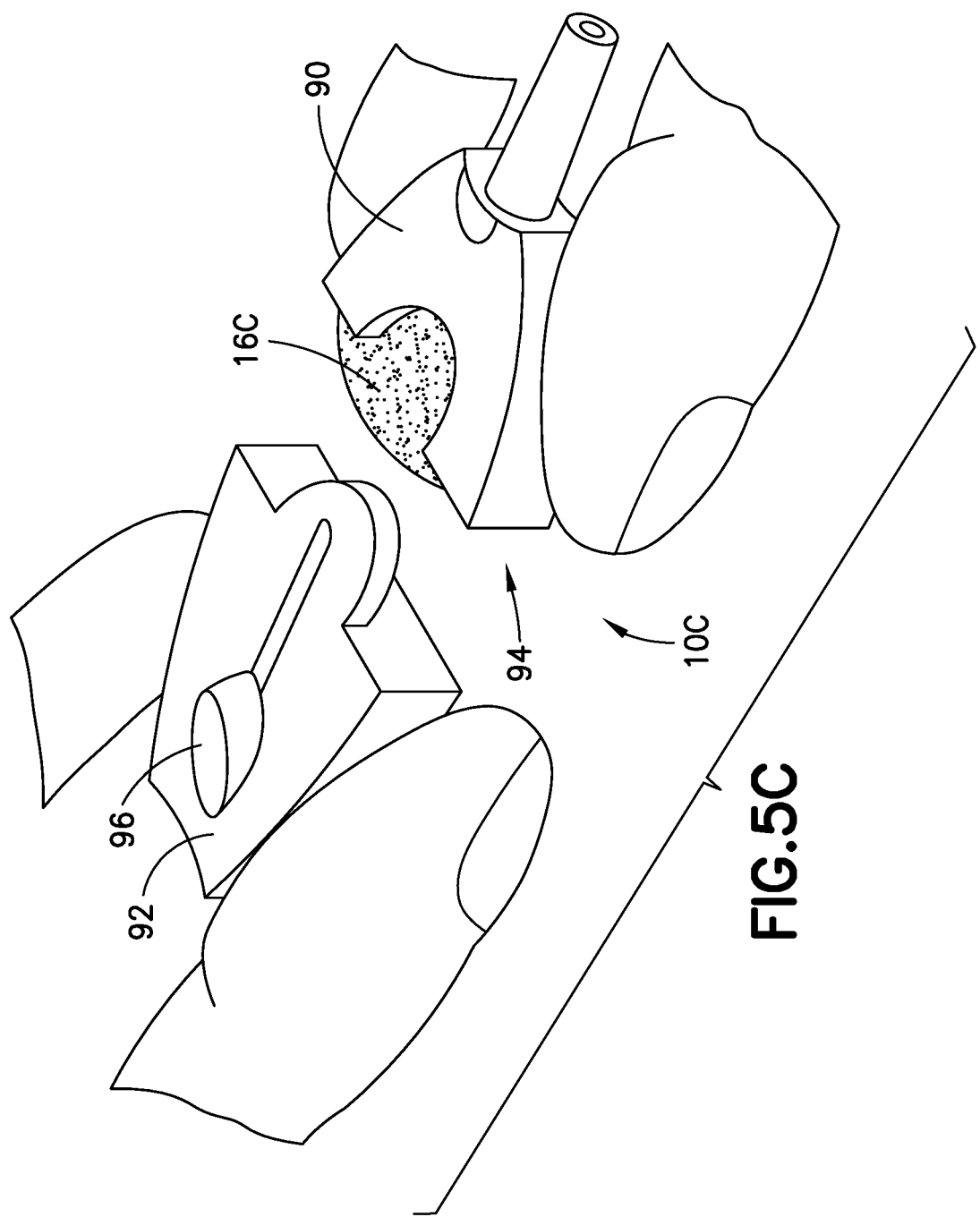

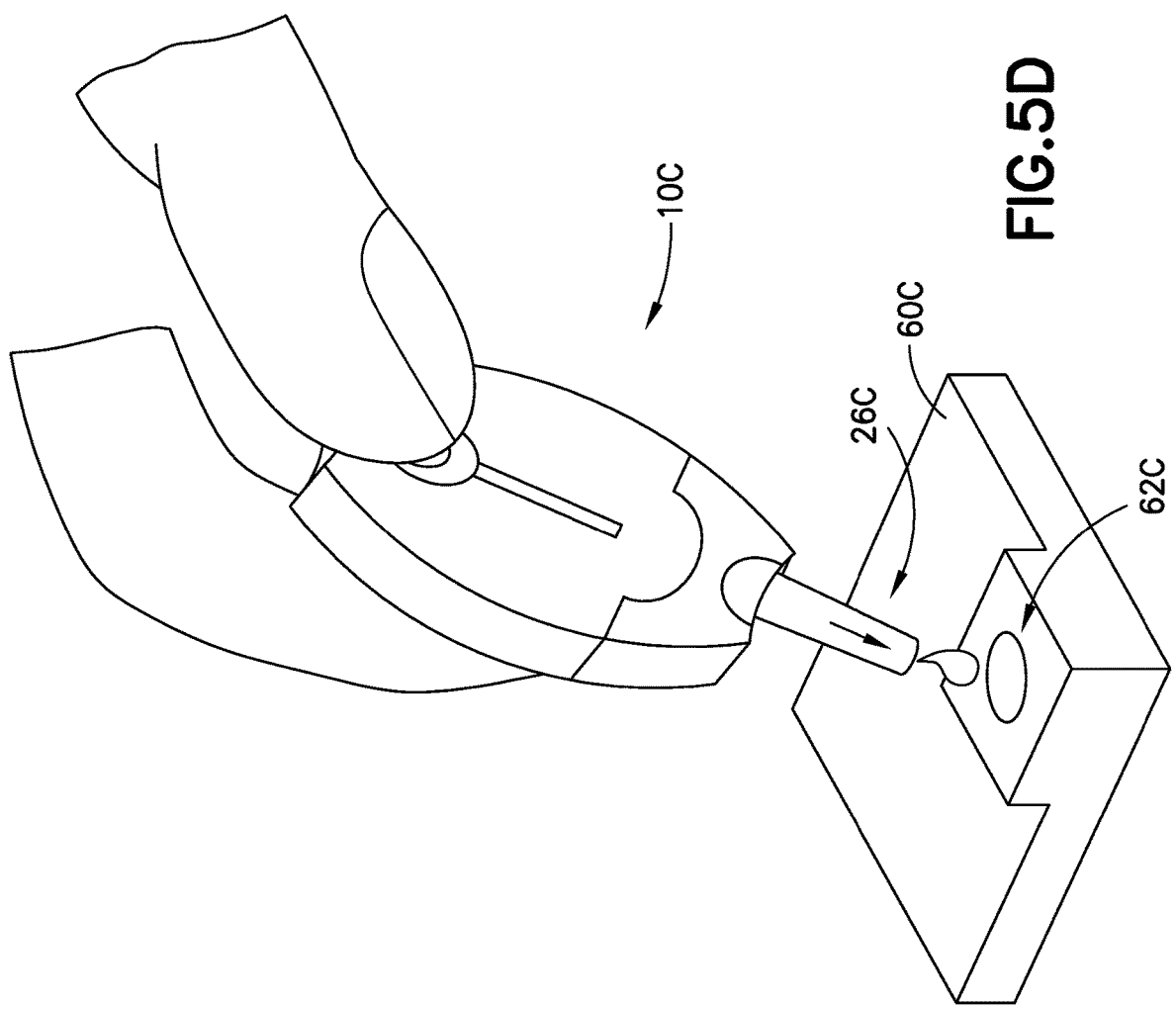

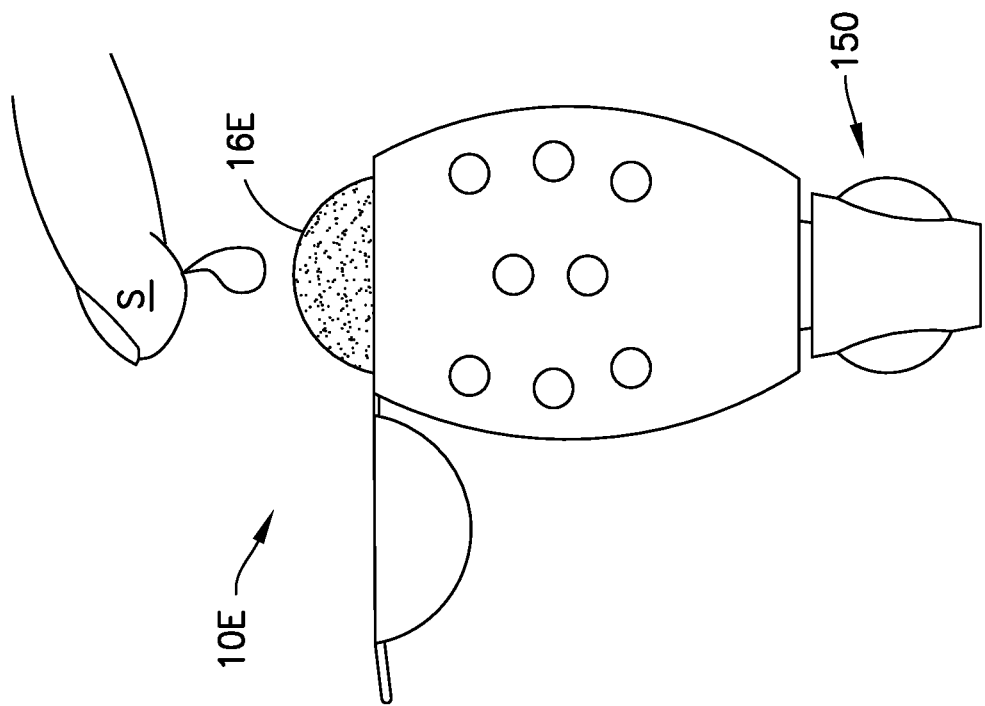
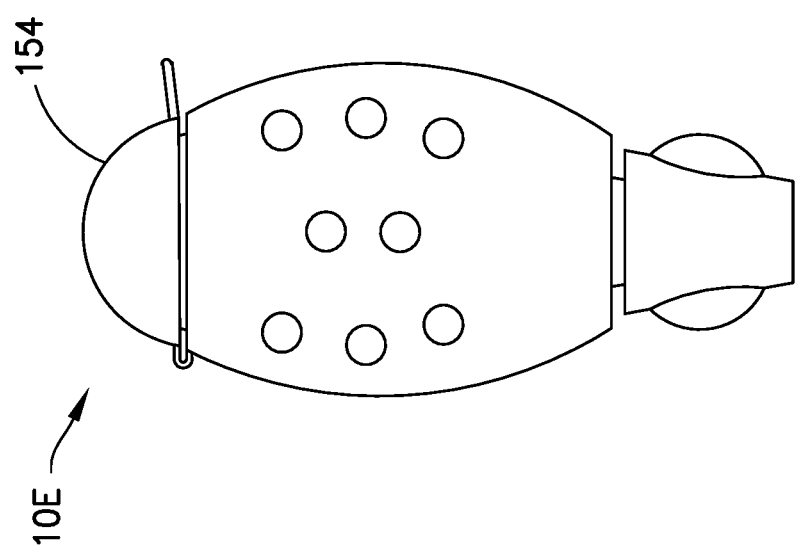
FIG. 7B
FIG. 7A

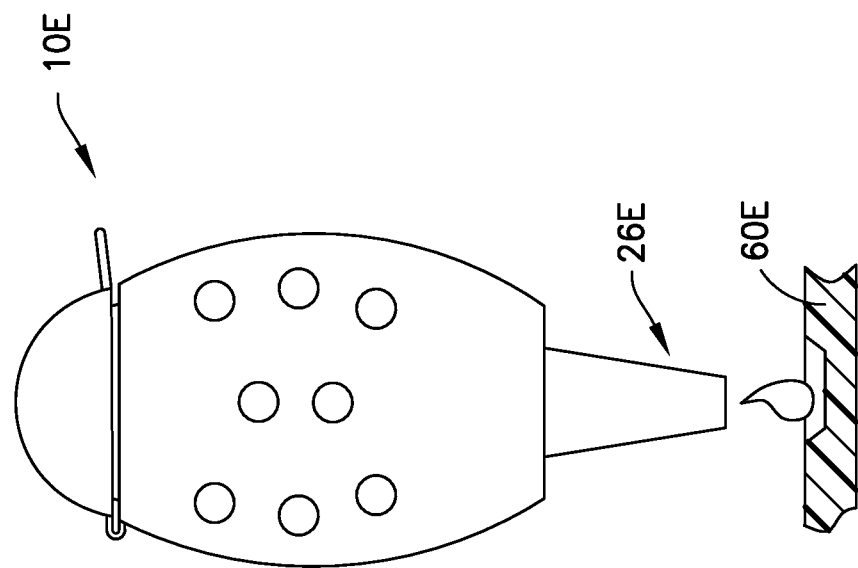
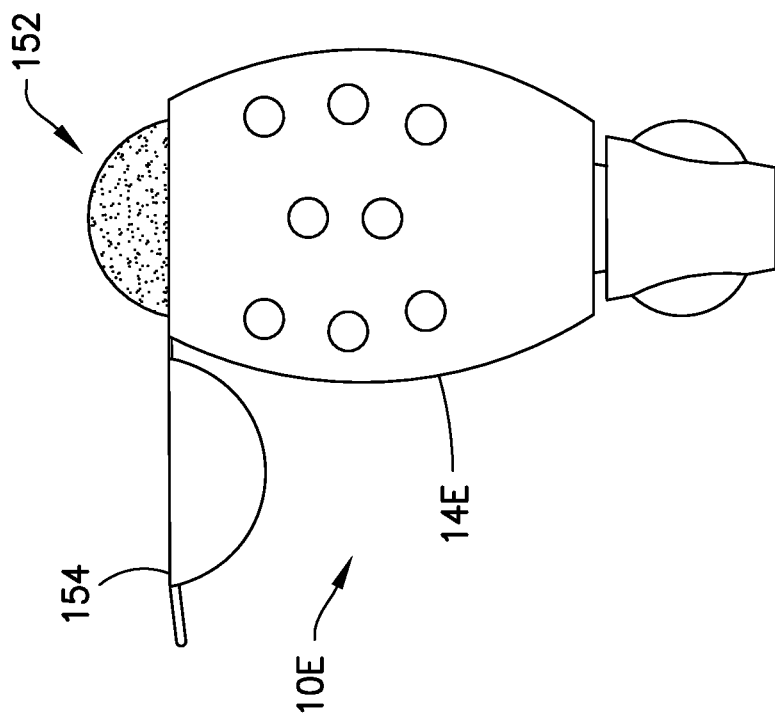
FIG.7D
FIG.7C

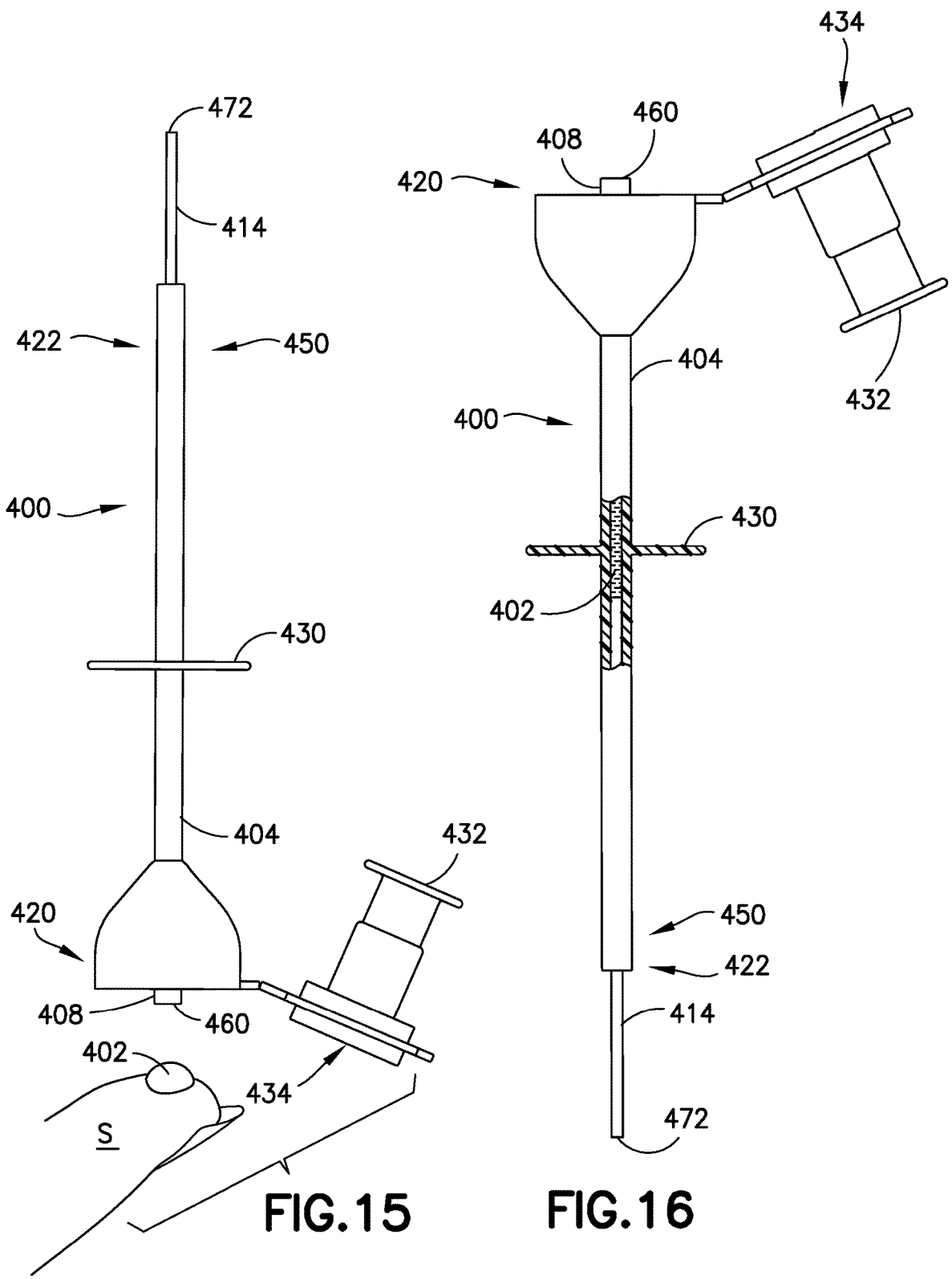

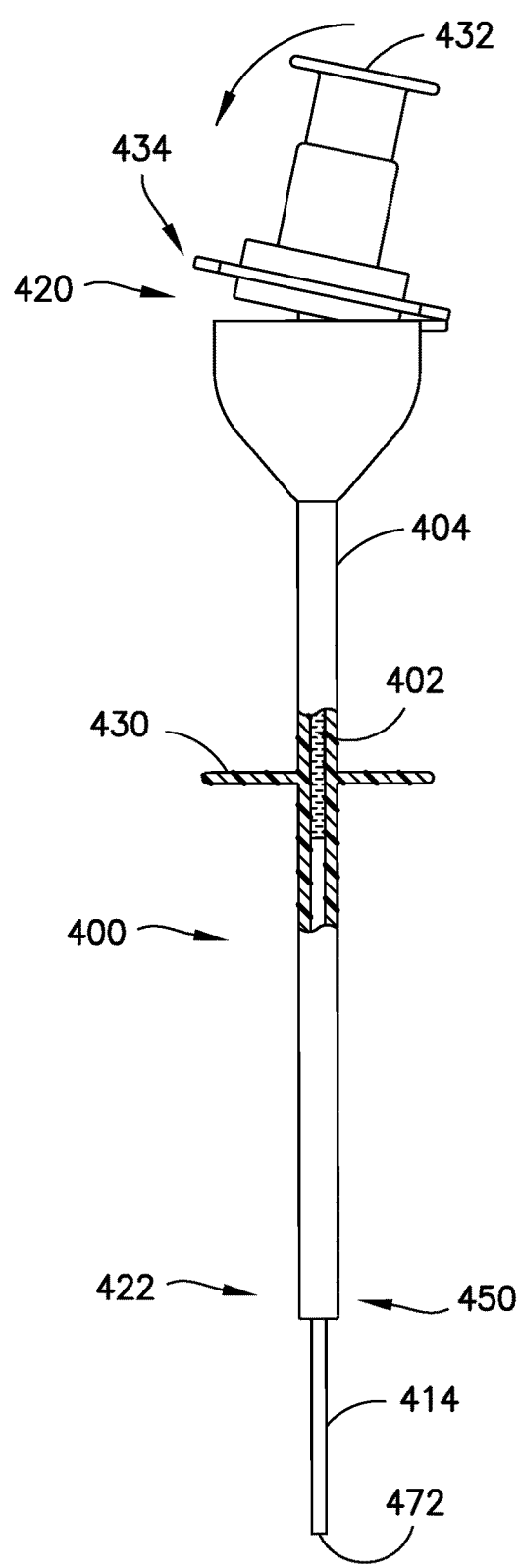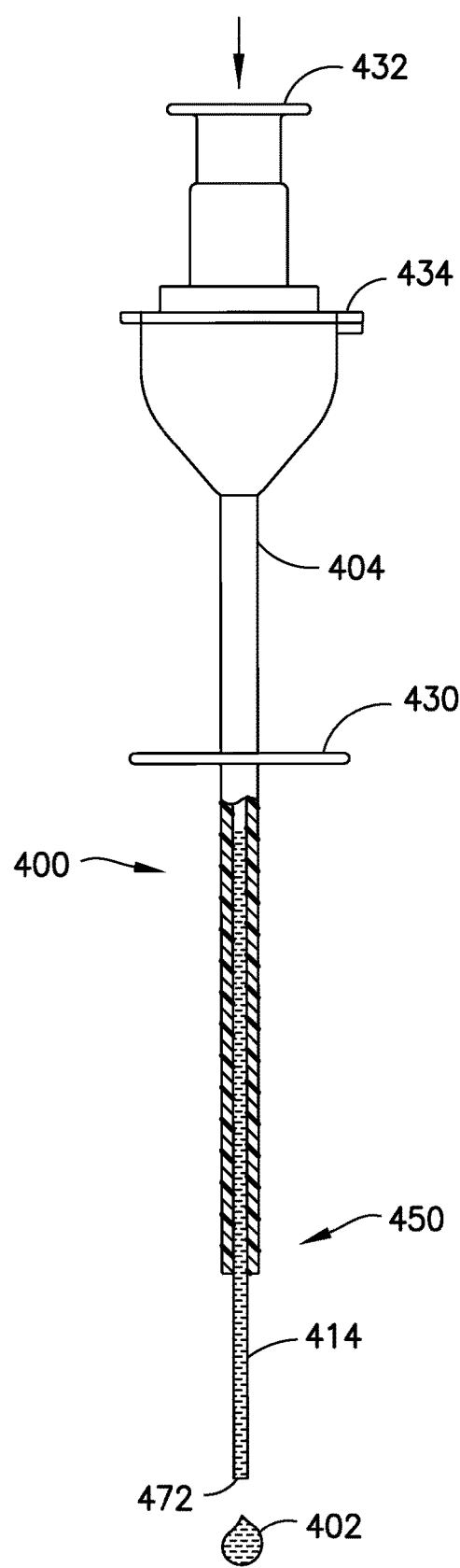
FIG. 17
FIG. 18

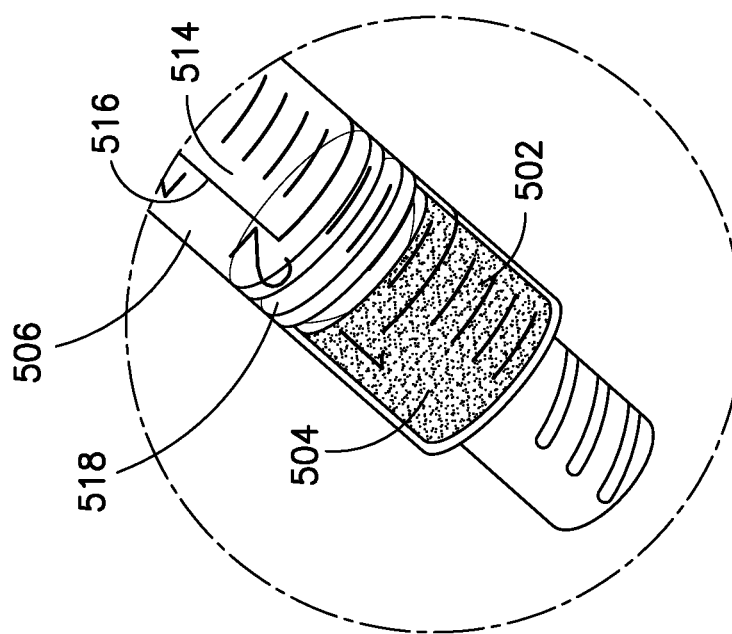
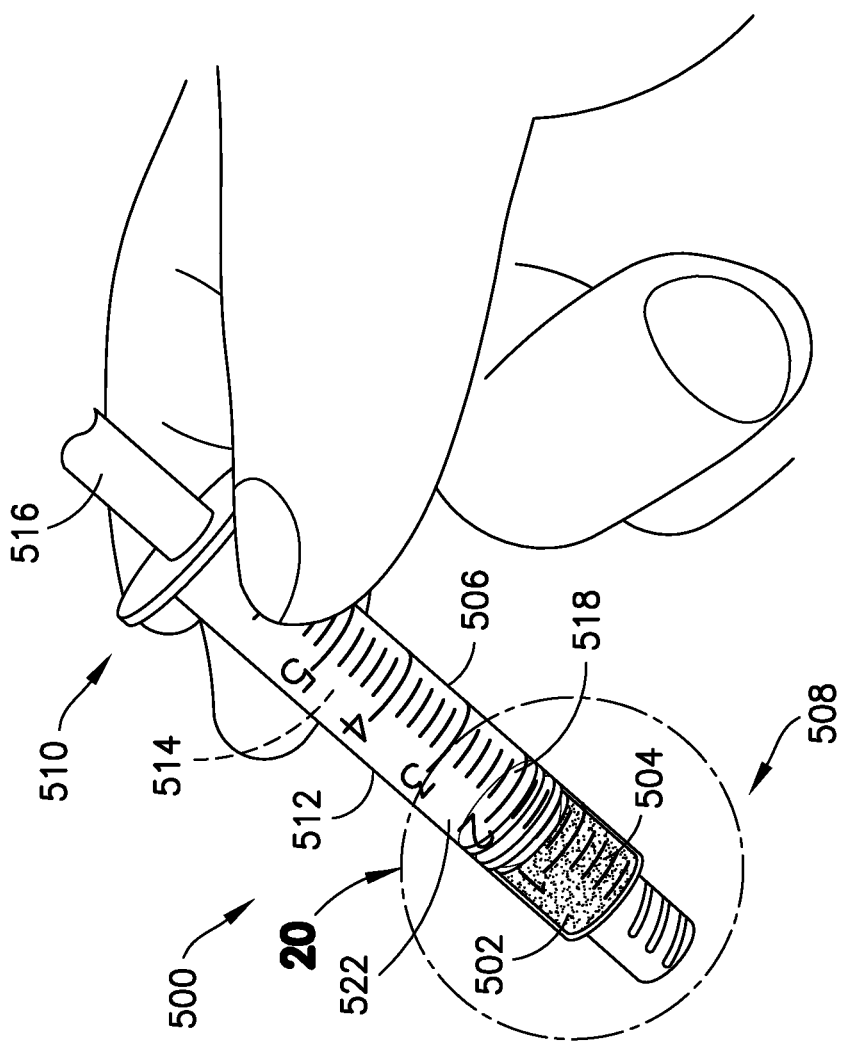
FIG.20
FIG.19

BLOOD SAMPLE MANAGEMENT USING OPEN CELL FOAM

CROSS-REFERENCE TO RELATED APPLICATIONS

This application is a divisional application of U.S. application Ser. No. 14/861,136, entitled "Blood Sample Management Using Open Cell Foam" filed Sep. 22, 2015, which claims priority to U.S. Provisional Application Ser. No. 62/063,536, entitled "Blood Sample Management Using Open Cell Foam" filed Oct. 14, 2014, and U.S. Provisional Application Ser. No. 62/207,618, entitled "Blood Sample Management Using Open Cell Foam" filed Aug. 20, 2015, the entire disclosures of each of which are herein incorporated by reference.

BACKGROUND OF THE INVENTION

1. Field of the Disclosure

The present disclosure relates generally to a blood transfer device. More particularly, the present disclosure relates to a blood transfer device, a blood transfer and testing system, a lancet and blood transfer device, and a method of loading an anticoagulant.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Once collected, blood samples may be analyzed to obtain medically useful information including, for example, chemical composition, hematology, and coagulation.

Blood tests determine the physiological and biochemical states of the patient, such as disease, mineral content, drug effectiveness, and organ function. Blood tests may be performed in a clinical laboratory or at the point-of-care near the patient.

SUMMARY OF THE INVENTION

The present disclosure provides a blood transfer device adapted to receive a blood sample. The blood transfer device includes a housing having a first end, a second end, a sidewall extending therebetween, and an actuation member movable between a first position and a second position. A deformable material is disposed within the housing and is deformable from an initial position in which the material is adapted to hold the blood sample to a deformed position in which a portion of the blood sample is released from the material. A viscoelastic member is disposed within the housing between the material and the sidewall of the housing and between the material and the actuation member. The viscoelastic member is engaged with the actuation member and the material such that movement of the actuation member from the first position to the second position exerts a force on the viscoelastic member which redistributes the force evenly over the material and deforms the material from the initial position to the deformed position.

In accordance with an embodiment of the present invention, a specimen transfer device adapted to receive a sample includes a housing having a first end, a second end, a sidewall extending therebetween, and an actuation member movable between a first position and a second position. The device further includes a deformable material disposed within the housing, in which the material is deformable from an initial position in which the material is adapted to contain the sample, to a deformed position in which at least a portion of the sample is released from the material. The device also includes a viscoelastic member disposed within the housing between the material and the sidewall of the housing and between the material and the actuation member. The viscoelastic member is engaged with the actuation member and the material such that movement of the actuation member from the first position to the second position exerts a force on the viscoelastic member which deforms the material from the initial position to the deformed position.

In certain configurations, the deformable material includes pores. The device may also include a dry anticoagulant powder disposed within the pores of the material. The housing may also include a dispensing tip at the first end. Optimally, the housing includes a valve disposed within the dispensing tip, with the valve being transitionable between a closed position and an open position. With the material in the deformed position and the valve in the open position, the at least a portion of the sample may be released from the material and may flow through the dispensing tip.

In certain configurations, the viscoelastic member has a viscoelastic member hardness. The actuation member may also have an actuation member hardness. In certain configurations, the viscoelastic member hardness is less than the actuation member hardness. The actuation member may be located at the second end of the housing. Optionally, the actuation member may be a push button, and the sample may be blood.

In accordance with another embodiment of the present invention, a specimen transfer and testing system may include a specimen transfer device adapted to receive a sample. The specimen transfer device may include a housing having a first end, a second end, a sidewall extending therebetween, a dispensing tip at the first end, an actuation member at the second end, and a valve disposed within the dispensing tip. The actuation member may be movable between a first position and a second position, and the valve may be transitionable between a closed position and an open position. The specimen transfer device may also include a deformable material having pores and disposed within the housing, with the material deformable from an initial position in which the material is adapted to contain the sample to a deformed position in which at least a portion of the sample is released from the material. The specimen transfer device may also include a viscoelastic member disposed within the housing between the material and the sidewall of the housing and between the material and the actuation member. The viscoelastic member may be engaged with the actuation member and the material such that movement of the actuation member from the first position to the second position exerts a force on the viscoelastic member which deforms the material from the initial position to the deformed position. With the material in the deformed position and the valve in the open position, the portion of the sample released from the material may flow through the dispensing tip. The specimen transfer and testing system may also include a sample testing device having a receiving port adapted to receive the dispensing tip of the specimen transfer device for closed transfer of at least a portion of the sample from the specimen transfer device to the sample testing device.

In certain configurations, the specimen transfer device further includes a dry anticoagulant powder within the pores of the material. The viscoelastic member may have a viscoelastic member hardness, the actuation member may have an actuation member hardness, and the viscoelastic member hardness may be less than the actuation member hardness. In certain configurations, the actuation member is a push button. In other configurations, the specimen is blood.

In accordance with yet another embodiment of the present invention, a lancet and specimen transfer device includes a lancet housing having a forward end, a rearward end, and a puncturing element, the puncturing element at least partially disposed within the lancet housing and adapted for movement between a pre-actuated position wherein the puncturing element is retained within the lancet housing and a puncturing position wherein at least a portion of the puncturing element extends through the forward end of the lancet housing. The lancet and specimen transfer device further includes a specimen transfer device engageable with the rearward end of the lancet housing.

In accordance with another embodiment of the present invention, a blood transfer device adapted to receive a blood sample includes a housing having a first end, a second end, and an actuation member transitionable between a first position and a second position. The blood transfer device further includes an open cell foam material disposed within the housing and having a dry anticoagulant powder therein.

In certain configurations, the blood transfer device also includes a capillary tube in fluid communication with the open cell foam material. The housing may also include a lid movable between a closed position in which the open cell foam material is sealed within the housing and an open position in which a portion of the open cell foam material is exposed. The capillary tube may be adapted to receive the blood sample after the blood sample is mixed with the dry anticoagulant powder within the open cell foam material. The capillary tube may include a dispensing tip.

Movement of the actuation member from the first position to the second position may dispense the blood sample through the dispensing tip of the capillary tube. The first capillary tube may be disposed between the first end of the housing and the open cell foam material. The device may also include a second capillary tube in fluid communication with the open cell foam material, with the second capillary tube disposed between the second end of the housing and the open cell foam material. The second capillary tube may be adapted to receive the blood sample after the blood sample is mixed with the dry anticoagulant powder within the open cell foam material. Movement of the actuation member from the first position to the second position may dispense the blood sample through a dispensing tip of the second capillary tube. At least one of an internal surface of the first capillary tube and an internal surface of the second capillary tube may include an anticoagulant coating. The first capillary tube and the second capillary tube may have different lengths. Optionally, the first capillary tube and the second capillary tube may have different internal diameters.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 1A is a schematic representation of a deformable material of a blood transfer device in accordance with an embodiment of the present invention.

FIG. 1B is a schematic representation of a deformable material of a blood transfer device in accordance with an embodiment of the present invention.

FIG. 1C is a schematic representation of a deformable material of a blood transfer device in accordance with an embodiment of the present invention.

FIG. 1D is a schematic representation of a deformable material and a viscoelastic member of a blood transfer device in accordance with an embodiment of the present invention.

FIG. 1E is a schematic representation of a deformable material and a viscoelastic member of a blood transfer device in accordance with an embodiment of the present invention.

FIG. 4C is a perspective view of a step of using the blood transfer device of FIG. 4A in accordance with an embodiment of the present invention.

FIG. 5A is a front view of a blood transfer device in accordance with an embodiment of the present invention.

FIG. 5B is a perspective view of a step of using the blood transfer device of FIG. 5A in accordance with an embodiment of the present invention.

FIG. 5C is a perspective view of a step of using the blood transfer device of FIG. 5A in accordance with an embodiment of the present invention.

FIG. 5D is a perspective view of a step of using the blood transfer device of FIG. 5A in accordance with an embodiment of the present invention.

FIG. 7A is a front view of a blood transfer device in accordance with an embodiment of the present invention.

FIG. 7B is a front view of a step of using the blood transfer device of FIG. 7A in accordance with an embodiment of the present invention.

FIG. 7C is a front view of a step of using the blood transfer device of FIG. 7A in accordance with an embodiment of the present invention.

FIG. 7D is a front view of a step of using the blood transfer device of FIG. 7A in accordance with an embodiment of the present invention.

FIG. 15 is a front view of a step of using the blood transfer device of FIG. 14 in accordance with an embodiment of the present invention.

FIG. 16 is a front view of a step of using the blood transfer device of FIG. 14 in accordance with an embodiment of the present invention.

FIG. 17 is a front view of a step of using the blood transfer device of FIG. 14 in accordance with an embodiment of the present invention.

FIG. 18 is a front view of a step of using the blood transfer device of FIG. 14 in accordance with an embodiment of the present invention.

FIG. 19 is a perspective view of a syringe assembly in accordance with an embodiment of the present invention.

FIG. 20 is a close-up partial perspective view of the syringe assembly of FIG. 19 in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 2:
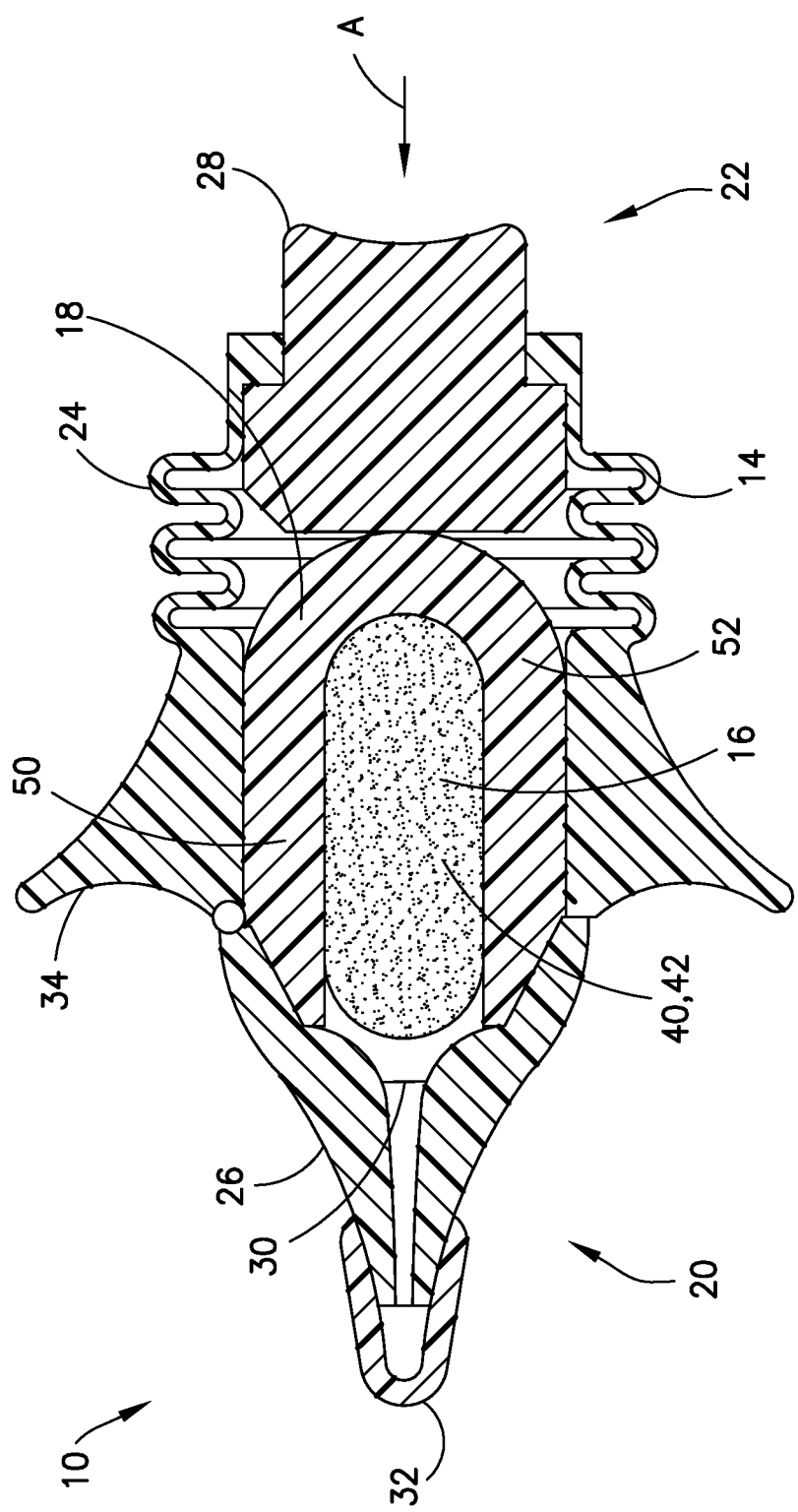
FIG. 2 is a cross-sectional front view of a blood transfer device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

FIG. 2 illustrates an exemplary embodiment of a blood transfer device of the present disclosure. Referring to FIG. 2, a blood transfer device 10 adapted to receive a blood sample 12 (FIG. 3B) includes a housing or body 14, a deformable material 16, and a viscoelastic member 18.

In one embodiment, housing 14 includes a first end 20, a second end 22, a sidewall 24 extending therebetween, a dispensing tip 26 at the first end 20, an actuation member 28 at the second end 22, a valve 30, a cap 32, and a finger flange 34.

The blood transfer device 10 may include an actuation member 28 that is movable between a first position and a second position. In one embodiment, the actuation member 28 is located at the second end 22 of the housing 14. In one embodiment, the actuation member 28 is a push button. The actuation member has an actuation member hardness.

The blood transfer device 10 may include a cap 32 for protectively covering the blood transfer device 10 prior to use thereof. In one embodiment, the cap 32 protectively covers the dispensing tip 26 of the blood transfer device 10 prior to use thereof.

The blood transfer device 10 may include a valve 30 that is transitionable between a closed position and an open position. In one embodiment, the valve 30 is disposed within the dispensing tip 26. With the valve 30 in an open position, a portion of the blood sample 12 that is released from the material 16 is able to flow through the dispensing tip 26. In one embodiment, a portion of the blood sample 12 that is released from the material 16 is able to flow through the dispensing tip 26 to a blood testing device 60. With the valve 30 in a closed position, no portion of the blood sample 12 is able to flow from the blood transfer device 10.

Referring to FIGS. 3A-7D, a blood testing device 60 includes a receiving port 62 adapted to receive the dispensing tip 26 of the blood transfer device 10. The blood testing device 60 is adapted to receive the dispensing tip 26 of the blood transfer device 10 for closed transfer of a portion of the blood sample 12 (FIG. 3C) from the material 16 of the blood transfer device 10 to the blood testing device 60. The blood testing device 60 is adapted to receive the blood sample 12 to analyze the blood sample and obtain test results. In one embodiment, the blood testing device 60 is a point-of-care testing device.

In one embodiment, material 16 includes pores 40 (FIG. 2) and is disposed within the housing 14 of the blood transfer device 10. The material 16 is deformable from an initial position in which the material 16 is adapted to hold the blood sample 12 to a deformed position in which a portion of the blood sample 12 is released from the material 16. In one embodiment, the material 16 includes a dry anticoagulant powder 42 within the pores 40 of the material 16. A method of loading an anticoagulant to a material 16 having pores 40 is described in more detail below.

In one embodiment, the material 16 is a sponge material. In one embodiment, the material 16 is an open cell foam. In one embodiment, the open cell foam is treated with an anticoagulant, as described in detail below, to form a dry anticoagulant powder finely distributed throughout the pores 40 of the material 16. The open cell foam may be loaded with a blood sample. The blood gets soaked into the open cell foam based on capillary principles. As the blood is loaded into the open cell foam, the blood is exposed to the anticoagulant powder throughout the internal micro pore structure of the open cell foam. Once the open cell foam is loaded with the blood, the open cell foam may be deformed, e.g., compressed, to squeeze-out a stabilized blood sample. In one embodiment, the stabilized blood sample may be transferred to a diagnostic instrument such as a blood testing device, a point-of-care testing device, or similar analytical device.

In one embodiment, the material 16 is a soft deformable open cell foam that is inert to blood. In one embodiment, the open cell foam may be a melamine foam, such as Basotect® foam commercially available from BASF. In another embodiment, the open cell foam may consist of a formaldehyde-melamine-sodium bisulfite copolymer. The open cell foam may be a flexible, hydrophilic open cell foam that is resistant to heat and many organic solvents. In one embodiment, the open cell foam may be a sponge material.

A method of loading an anticoagulant to a material 16 having pores 40 will now be discussed. In one embodiment, the method includes soaking the material 16 in a liquid solution of the anticoagulant and water; evaporating the water of the liquid solution; and forming a dry anticoagulant powder 42 within the pores 40 of the material 16.

The method of the present disclosure enables precisely controlled loading of an anticoagulant into the material 16 by soaking it with an anticoagulant and water solution and then drying the material 16 to form a finely distributed dry anticoagulant powder 42 throughout the pores 40 of the material 16.

Anticoagulants such as Heparin or EDTA (Ethylene Diamine Tetra Acetic Acid) as well as other blood stabilization agents could be introduced into the material 16 as a liquid solution by soaking the material 16 in the liquid solution of a desired concentration. After evaporating the liquid phase, e.g., evaporating the water from a water and Heparin solution, a dry anticoagulant powder may be formed and finely distributed throughout the internal structure of the material 16. For example, the dry anticoagulant powder may be finely distributed throughout the pores 40 of the material 16. In a similar manner, the material 16 could be treated to provide a hydrophobic, hydrophilic, or reactive internal pore surface.

In one embodiment, the viscoelastic member 18 is disposed within the housing 14 of the blood transfer device 10 between the material 16 and the sidewall 24 of the housing 14 and between the material 16 and the actuation member 28. For example, referring to FIG. 2, the viscoelastic member 18 includes a first portion 50 that is disposed between the material 16 and the sidewall 24 of the housing 14 and a second portion 52 that is disposed between the material 16 and the actuation member 28.

Viscoelastic member 18 of an exemplary embodiment is preferably made of a pliable material, such as a soft elastomer, for example. In one exemplary embodiment, viscoelastic member 18 is made from a viscoelastic material such as silicone or a thermoplastic elastomer (TPE). The viscoelastic member 18 serves as an intermediate member between the material 16 and the rigid surrounding components, e.g., the sidewall 24 of the housing 14 and the actuation member 28. In one embodiment, the viscoelastic member 18 serves as a damper or a soft viscoelastic damper. The viscoelastic member 18 uniformly redistributes the external imposed strain to the material 16 via the actuation member 28 as described below. In this manner, the viscoelastic member 18 minimizes blood hemolysis due to localized excessive deformation of the material 16. Additionally, the viscoelastic member 18 controls the speed of the deformation of the material 16 and mitigates the rate of the force applied to deform the material 16 via the actuation member 28.

The viscoelastic member 18 has a viscoelastic member hardness. The viscoelastic member hardness is less than the actuation member hardness. In one embodiment, the viscoelastic member hardness of the material that forms viscoelastic member 18 may have a hardness value on the Shore Durometer scale in the type A range for soft elastomers. In one exemplary embodiment, viscoelastic member 18 has a hardness of approximately Shore A 5.

The blood transfer device 10 may include a finger flange 34. When it is desired to expel or deliver a portion of the blood sample 12 from the material 16, the blood transfer device 10 is grasped with the user's thumb on the actuation member 28 and with the user's fingers extending around the finger flange 34. In this manner, the blood transfer device 10 is grasped by a user in a well-known and well recognized manner similar to the operation of a conventional hypodermic syringe. Next, the user effects a squeezing movement between the thumb on the actuation member 28 and the fingers grasping the finger flange 34, thereby causing the actuation member 28 to move in a direction generally along arrow A (FIG. 2) from a first position to a second position.

The viscoelastic member 18 is engaged with the actuation member 28 and the material 16 such that movement of the actuation member 28 from the first position to the second position exerts a force on the viscoelastic member 18 which redistributes the force evenly over the material 16 and deforms the material 16 from the initial position to the deformed position. In this manner, the viscoelastic member 18 minimizes blood hemolysis due to localized excessive deformation of the material 16. Additionally, the viscoelastic member 18 controls the speed of the deformation of the material 16 and mitigates the rate of the force applied to deform the material 16 via the actuation member 28.

With the material 16 in the deformed position and the valve 30 of the housing 14 in the open position, the portion of the blood sample 12 released from the material 16 is able to flow through the dispensing tip 26.

FIGS. 3A-7D illustrate other exemplary embodiments. The embodiment illustrated in FIGS. 3A-3C includes similar components to the embodiment illustrated in FIG. 2, and the similar components are denoted by a reference number followed by the letter A. The embodiment illustrated in FIGS. 4A-4E also includes similar components to the embodiment illustrated in FIG. 2, and the similar components are denoted by a reference number followed by the letter B. The embodiment illustrated in FIGS. 5A-5D also includes similar components to the embodiment illustrated in FIG. 2, and the similar components are denoted by a reference number followed by the letter C. The embodiment illustrated in FIGS. 6A-6D also includes similar components to the embodiment illustrated in FIG. 2, and the similar components are denoted by a reference number followed by the letter D. The embodiment illustrated in FIGS. 7A-7D also includes similar components to the embodiment illustrated in FIG. 2, and the similar components are denoted by a reference number followed by the letter E. For the sake of brevity, these similar components and the similar steps of using blood transfer devices 10A-10E (FIGS. 3A-7D) will not all be discussed in conjunction with the embodiments illustrated in FIGS. 3A-7D.

Figure 3A:
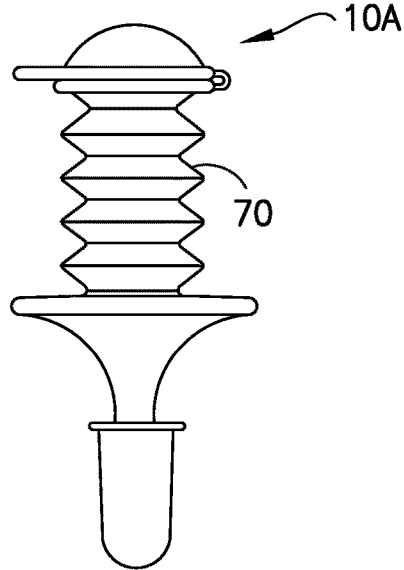
FIG. 3A is a front view of a blood transfer device in accordance with an embodiment of the present invention.
Figure 3B:
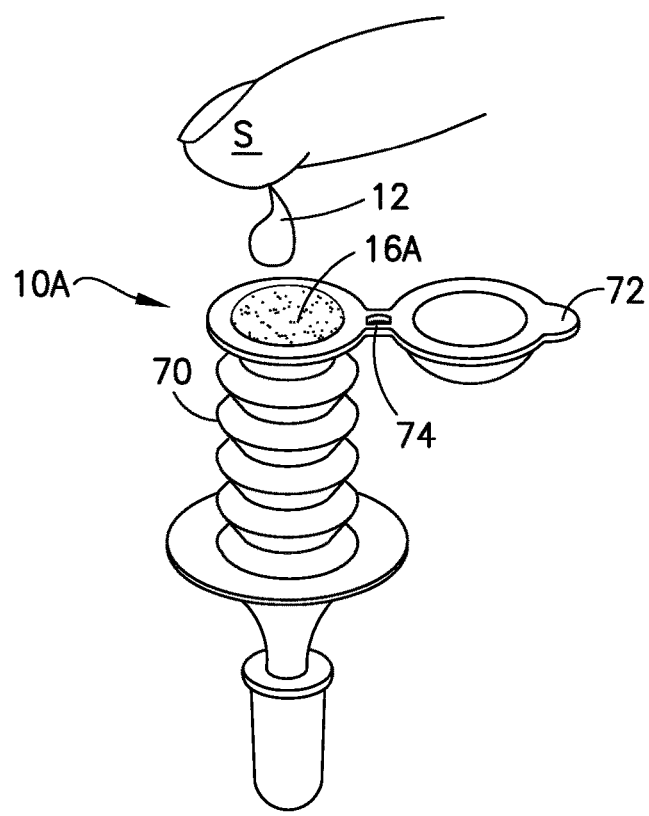
FIG. 3B is a perspective front view of the blood transfer device of FIG. 3A during a step of use in accordance with an embodiment of the present invention.
Figure 3C:
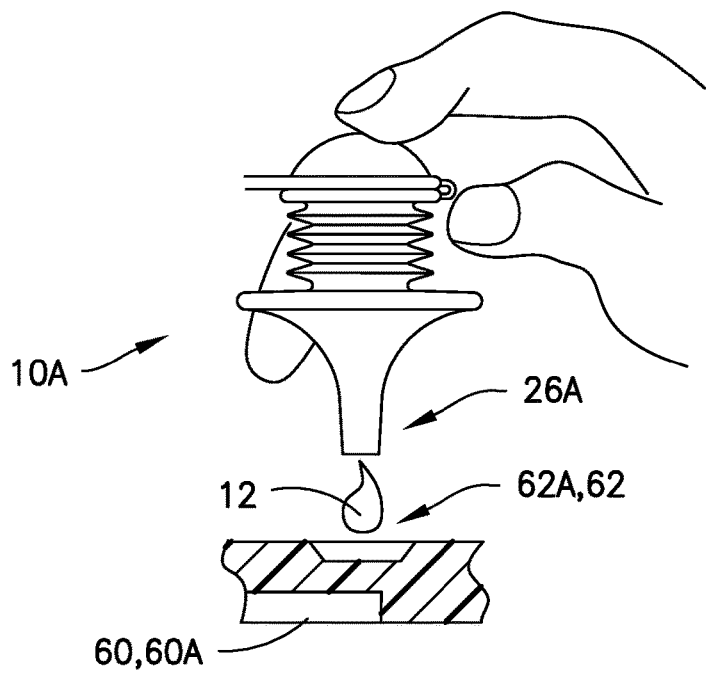
FIG. 3C is a front view of the blood transfer device of FIG. 3A during a step of use in accordance with an embodiment of the present invention.
Figure 4B:
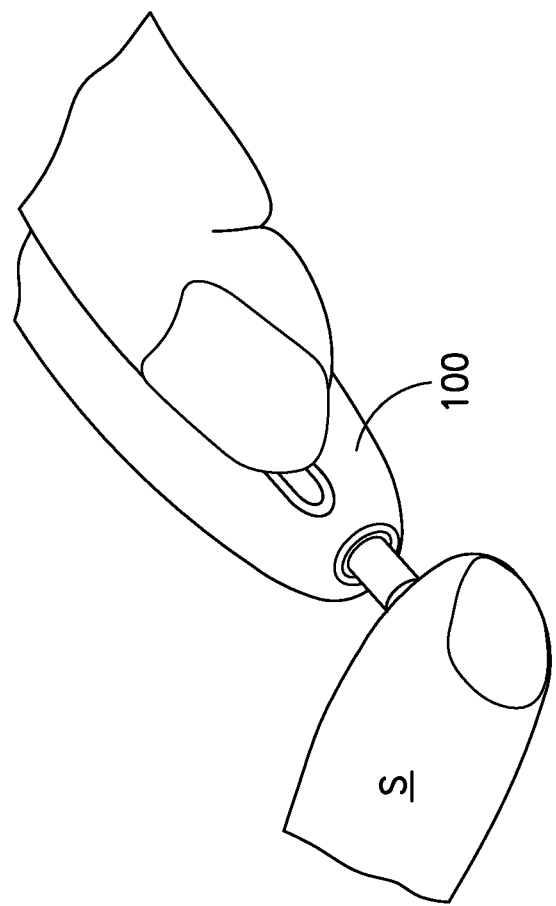
FIG. 4B is a perspective view of a step of using the blood transfer device of FIG. 4A in accordance with an embodiment of the present invention.
Figure 4A:
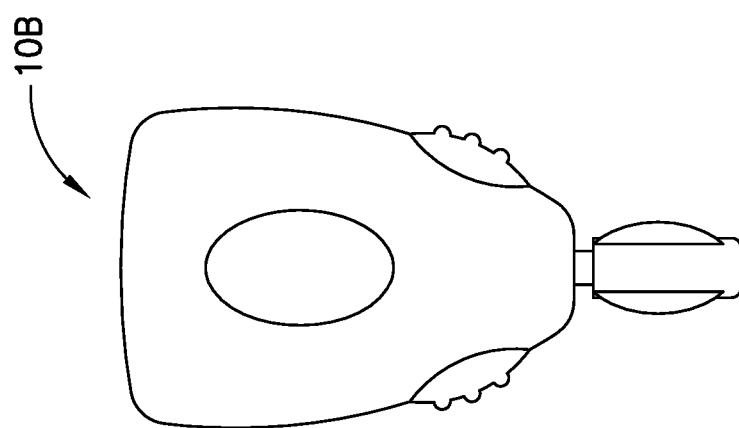
FIG. 4A is a front view of a blood transfer device in accordance with an embodiment of the present invention.
Figure 4D:
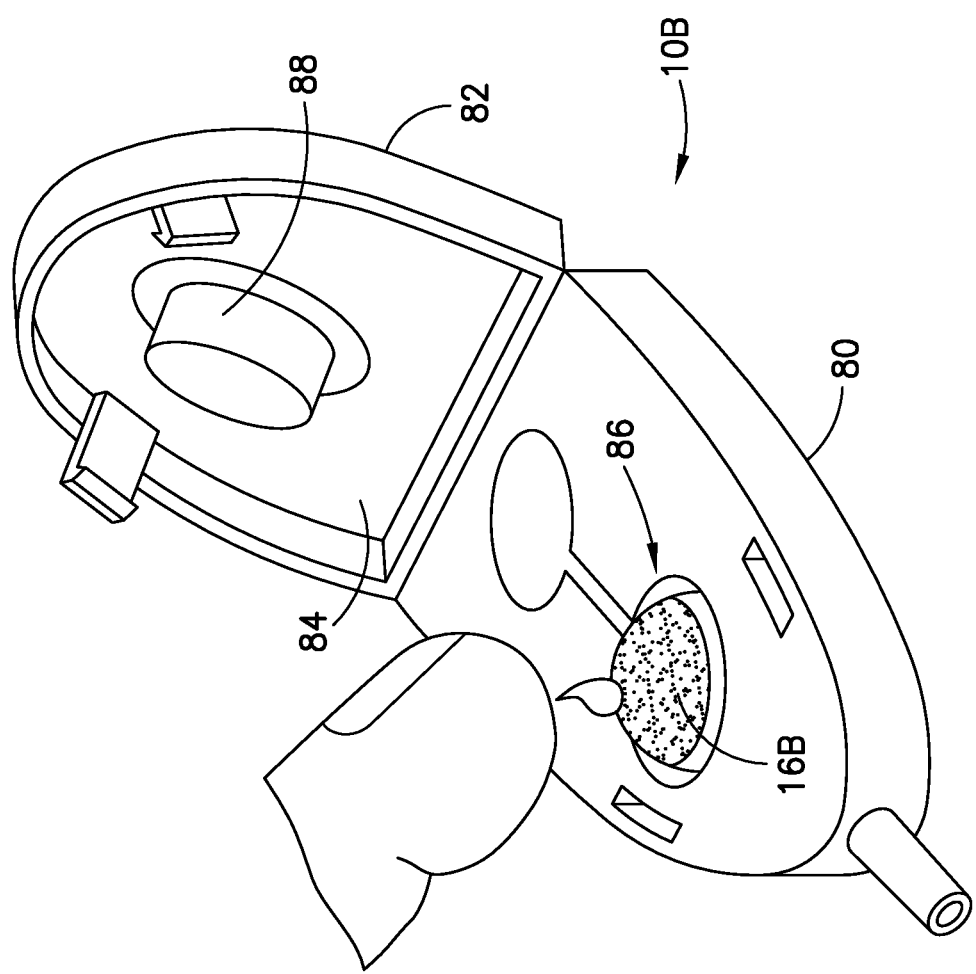
FIG. 4D is a perspective view of a step of using the blood transfer device of FIG. 4A in accordance with an embodiment of the present invention.
Figure 4E:
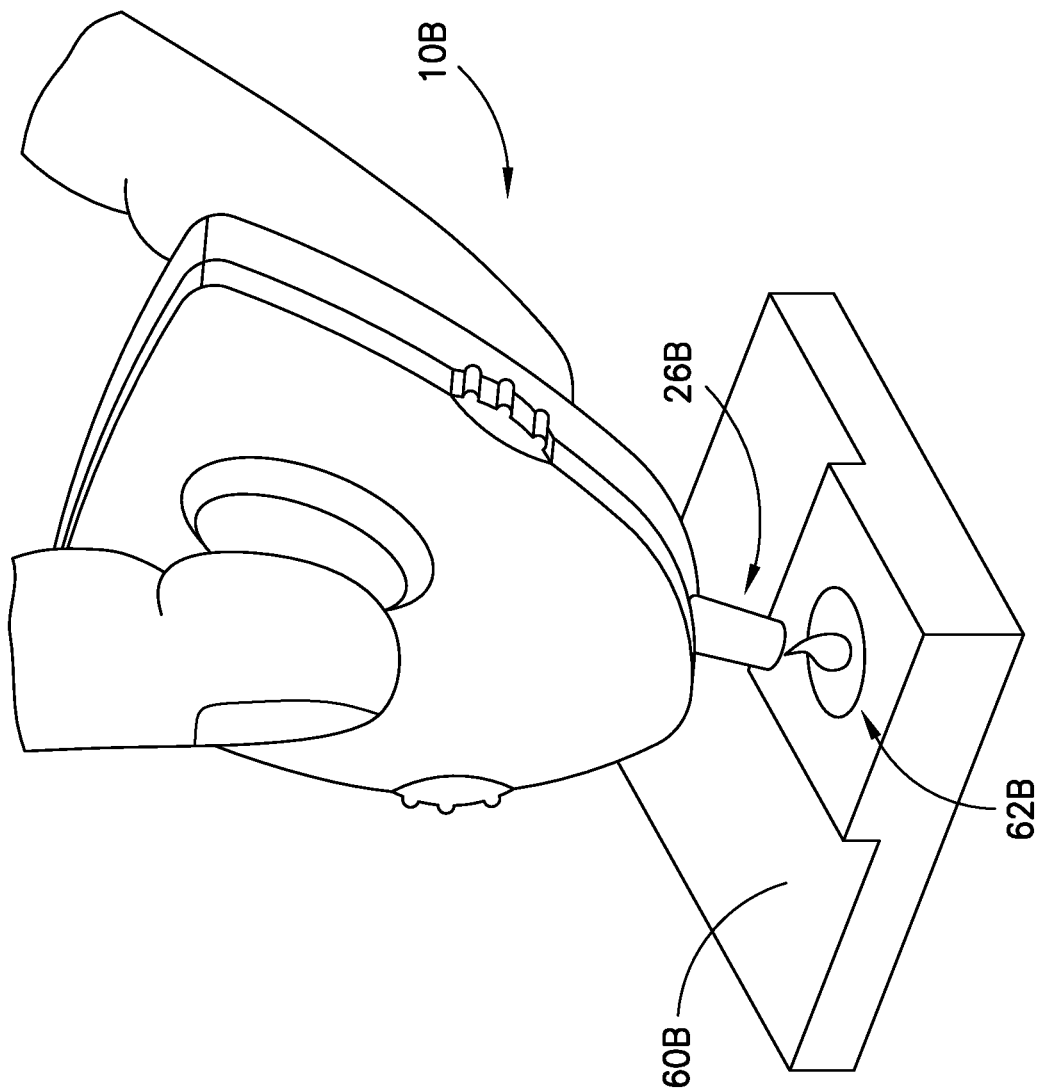
FIG. 4E is a perspective view of a step of using the blood transfer device of FIG. 4A in accordance with an embodiment of the present invention.
Figure 6A:
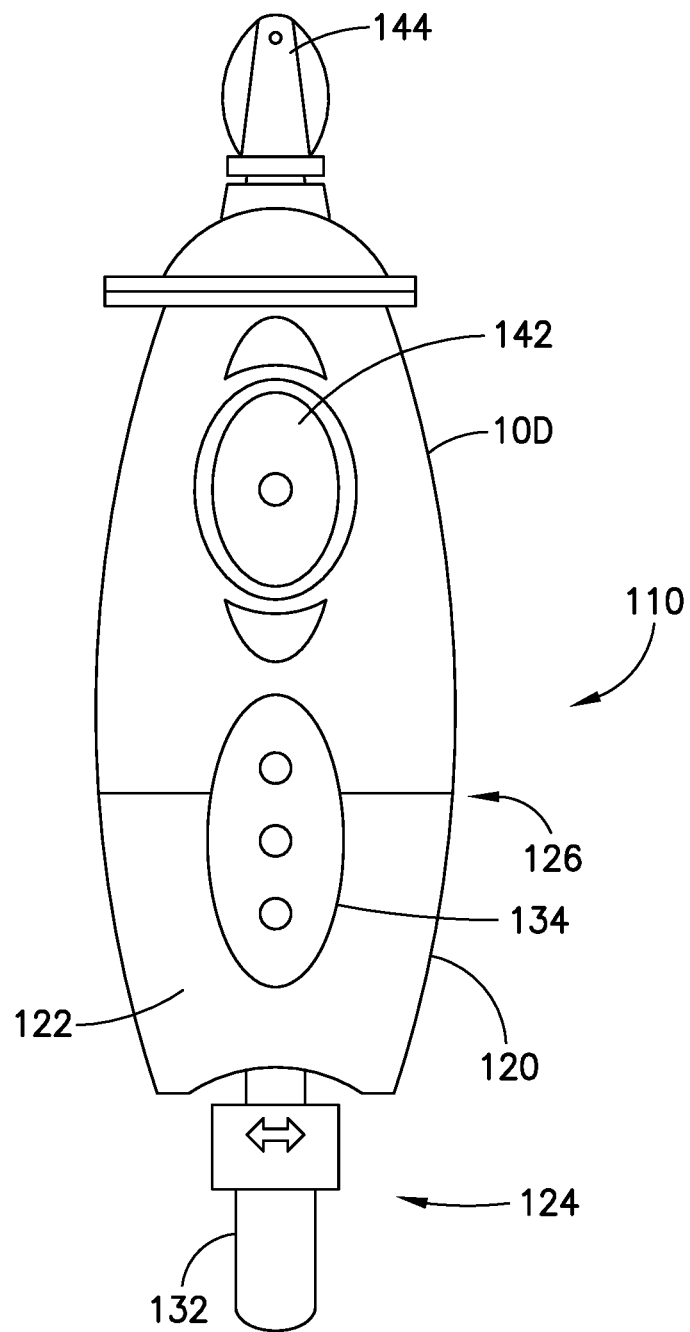
FIG. 6A is a front view of a lancet and blood transfer device in accordance with an embodiment of the present invention.
Figure 6B:
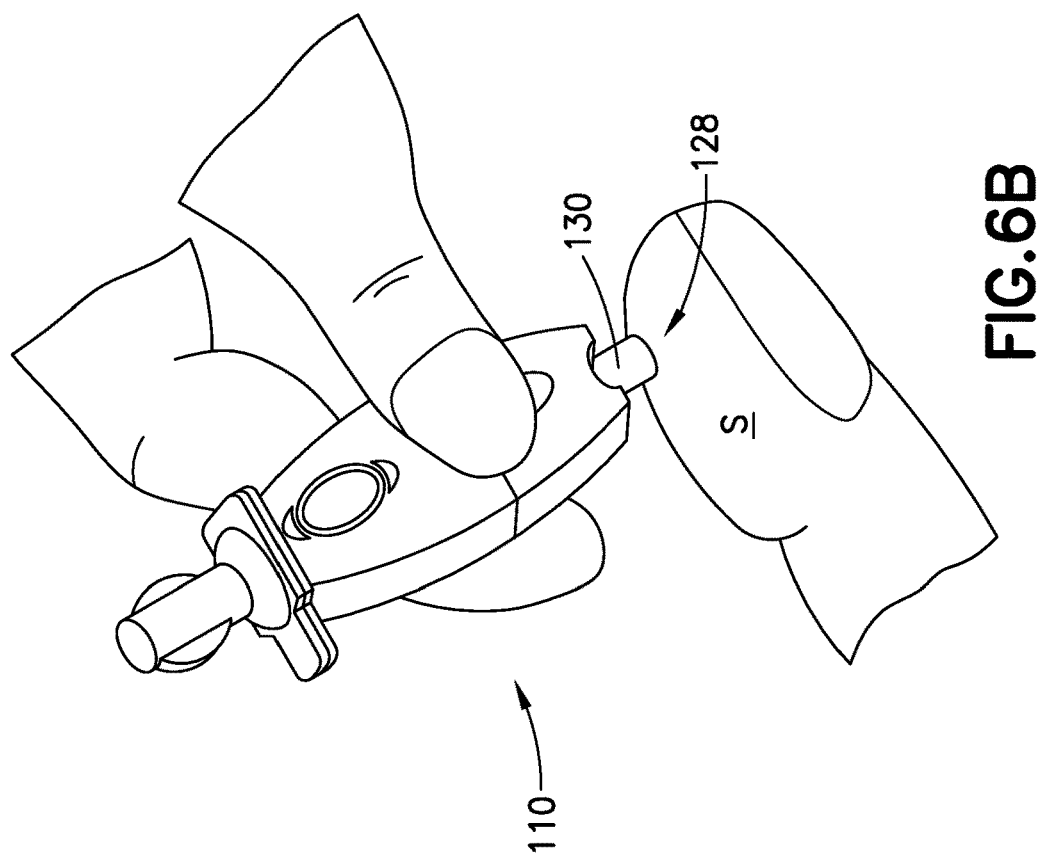
FIG. 6B is a perspective view of a step of using the lancet and blood transfer device of FIG. 6A in accordance with an embodiment of the present invention.
Figure 6C:
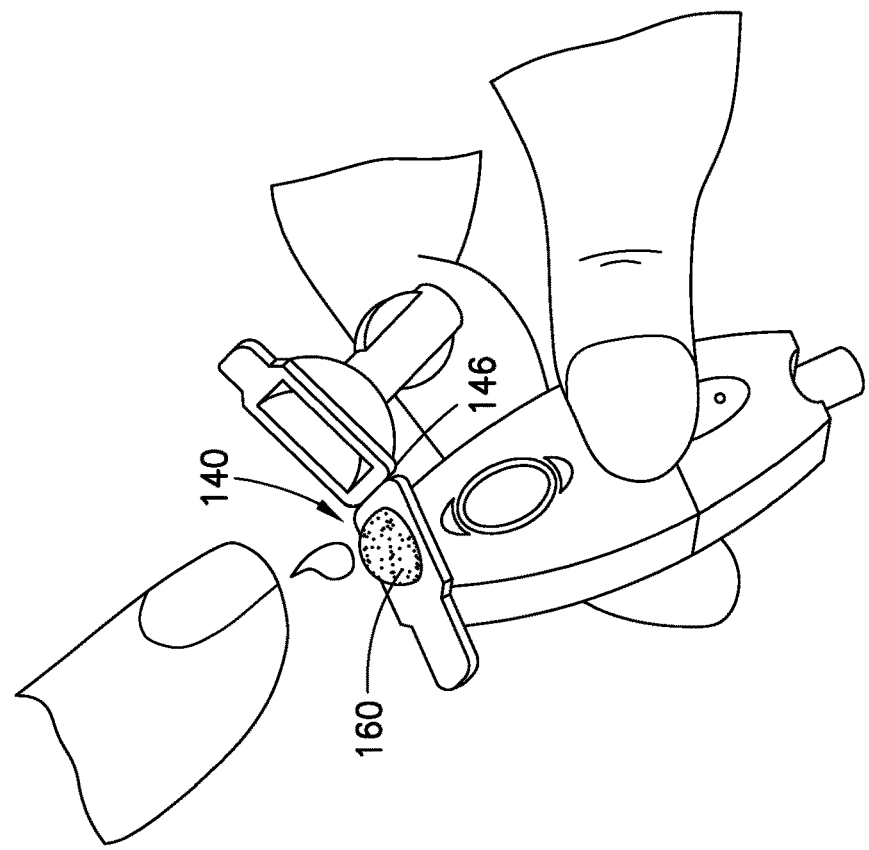
FIG. 6C is a perspective view of a step of using the lancet and blood transfer device of FIG. 6A in accordance with an embodiment of the present invention.
Figure 6D:
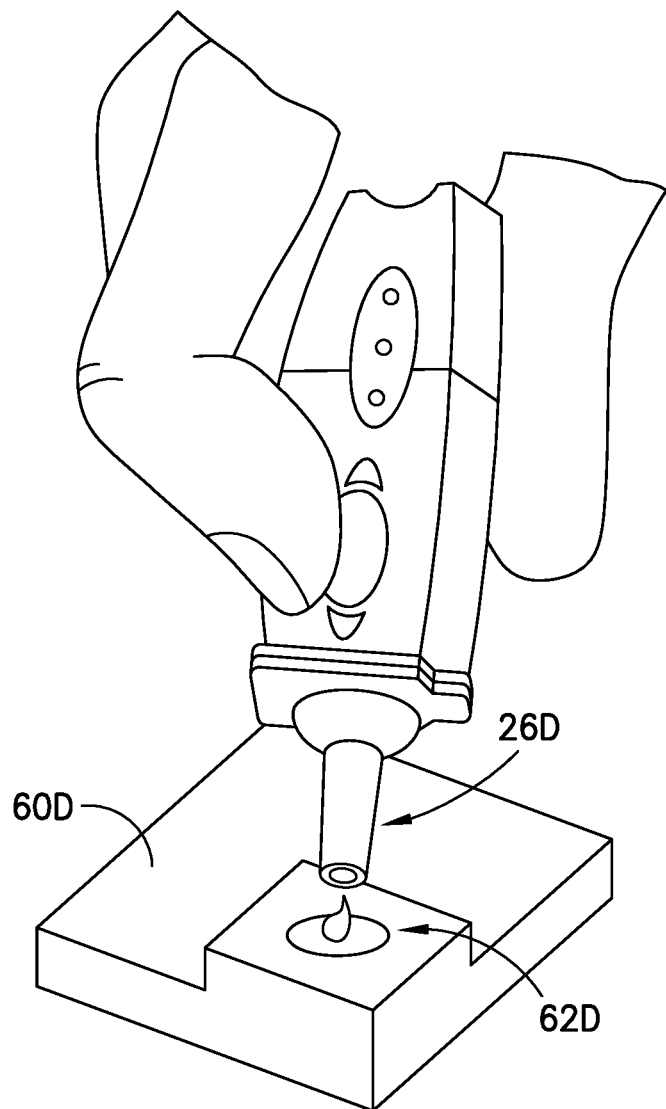
FIG. 6D is a perspective view of a step of using the lancet and blood transfer device of FIG. 6A in accordance with an embodiment of the present invention.

Referring to FIGS. 3A-3C, in one embodiment, blood transfer device 10A includes a body or bellows 70 and a cap 72 that is transitionable between an open position and a closed position. In one embodiment, the cap 72 is connected to the bellows 70 via a hinged portion 74.

During the use of blood transfer device 10A, a lancet device can be used to lance a skin surface S of a patient. Next, the cap 72 is moved to the open position to expose the material 16A. The blood transfer device 10A is then positioned such that the material 16A is placed adjacent a punctured skin surface S of a patient so that the blood sample 12 can be transferred to the material 16A. For example, the material 16A may touch the punctured skin surface S to soak up the blood sample 12. As the blood 12 is loaded into the material 16A, the blood 12 is exposed to the anticoagulant powder throughout the internal micro pore structure of the material 16A. Once the material 16A is loaded with the blood 12, the cap 72 is moved to the closed position and the material 16A is deformed, e.g., compressed, to squeeze out a stabilized blood sample 12. In one embodiment, the stabilized blood sample 12 may be transferred to a diagnostic instrument such as a blood testing device 60A.

Referring to FIGS. 4A-4E, in one embodiment, blood transfer device 10B includes a first body portion 80, a second body portion 82 connected to the first body portion 80 via a hinged portion 84, a chamber 86 within the first body portion 80 for receiving a material 16B, a protruding element 88 extending into the second body portion 82 towards the first body portion 80, and a sterile cap 89 in fluid communication with the chamber 86. The blood transfer device 10B is transitionable between an open position and a closed position.

During the use of blood transfer device 10B, a lancet device 100 can be used to lance a skin surface S of a patient. Next, the blood transfer device 10B is moved to the open position to expose the material 16B within the chamber 86. The blood transfer device 10B is then positioned such that the material 16B is placed adjacent a punctured skin surface S of a patient so that the blood sample 12 can be transferred to the material 16B. For example, the material 16B may touch the punctured skin surface S to soak up the blood sample 12. As the blood 12 is loaded into the material 16B, the blood 12 is exposed to the anticoagulant powder throughout the internal micro pore structure of the material 16B. Once the material 16B is loaded with the blood 12, the blood transfer device 10B is moved to the closed position and the material 16B is deformed, e.g., compressed, to squeeze out a stabilized blood sample 12. For example, the blood transfer device 10B can be squeezed so that the protruding element 88 deforms the material 16B thereby squeezing a stabilized blood sample 12 through the sterile cap 89. In one embodiment, the stabilized blood sample 12 may be transferred to a diagnostic instrument such as a blood testing device 60B.

Referring to FIGS. 5A-5D, in one embodiment, blood transfer device 10C includes a first body portion 90, a second body portion 92 removably connected to the first body portion 90, a chamber 94 within the first body portion 90 for receiving a material 16C, and a slide button 96 movably positioned within the second body portion 92. The blood transfer device 10C is transitionable between an open position and a closed position. The slide button 96 is transitionable between a first position and a second position.

During the use of blood transfer device 10C, a lancet device can be used to lance a skin surface S of a patient. Next, the second body portion 92 is removed from the first body portion 90 to open the blood transfer device 10C and expose the material 16C within the chamber 94. The blood transfer device 10C is then positioned such that the material 16C is placed adjacent a punctured skin surface S of a patient so that the blood sample 12 can be transferred to the material 16C. For example, the material 16C may touch the punctured skin surface S to soak up the blood sample 12. As the blood 12 is loaded into the material 16C, the blood 12 is exposed to the anticoagulant powder throughout the internal micro pore structure of the material 16C. Once the material 16C is loaded with the blood 12, the second body portion 92 is connected to the first body portion 90 to close the blood transfer device 10C and the material 16C is deformed, e.g., compressed, to squeeze out a stabilized blood sample 12. For example, the slide button 96 can be moved from the first position to the second position to compress the material 16C and squeeze a stabilized blood sample 12 through the dispensing tip 26C. In one embodiment, the stabilized blood sample 12 may be transferred to a diagnostic instrument such as a blood testing device 60C, as shown in FIG. 5D.

FIGS. 6A-6D illustrate another exemplary embodiment of the present disclosure. Referring to FIGS. 6A-6D, a lancet and blood transfer device 110 includes a lancet device 120 and a blood transfer device 10D.

In one embodiment, lancet device 120 includes a lancet housing 122 having a forward end 124 and a rearward end 126, a lancet structure 128 having a puncturing element 130, a protective cover 132, and a grip portion 134. In one embodiment, the lancet device 120 is a contact activated lancet device. The lancet device 120 may include the protective cover 132 for protectively covering the lancet device 120 prior to use thereof. The lancet housing 122 may include the grip portion 134 to generally improve the grip between the lancet housing 122 and the user's fingertips.

The lancet structure 128 is at least partially disposed within the lancet housing 122 and is adapted for movement between a pre-actuated position wherein the puncturing element 130 is retained within the lancet housing 122 and a puncturing position wherein at least a portion of the puncturing element 130 extends through the forward end 124 of the lancet housing 122.

Referring to FIGS. 6A-6D, in one embodiment, blood transfer device 10D includes a chamber 140 within the blood transfer device 10D for receiving a material 16D, a push button 142 transitionable between a first position and a second position, and a sterile cap 144 transitionable between an open position and a closed position. In one embodiment, the cap 144 is connected to the blood transfer device 10D via a hinged portion 146. In one embodiment, the blood transfer device 10D is connected to the rearward end 126 of the lancet housing 122 as shown in FIGS. 6A-6D.

During the use of lancet and blood transfer device 110, the lancet device 120 can be used to lance a skin surface S of a patient. Next, the cap 144 of the blood transfer device 10D is moved to the open position to expose the material 16D within the chamber 140.

The lancet and blood transfer device 110 is then positioned such that the material 16D is placed adjacent a punctured skin surface S of a patient so that the blood sample 12 can be transferred to the material 16D. For example, the material 16D may touch the punctured skin surface S to soak up the blood sample 12. As the blood 12 is loaded into the material 16D, the blood 12 is exposed to the anticoagulant powder throughout the internal micro pore structure of the material 16D. Once the material 16D is loaded with the blood 12, the cap 144 is moved to the closed position to close the blood transfer device 10D and the material 16D is deformed, e.g., compressed, to squeeze out a stabilized blood sample 12. For example, the push button 142 can be moved from the first position to the second position to compress the material 16D and squeeze a stabilized blood sample 12 through the dispensing tip 26D. In one embodiment, the stabilized blood sample 12 may be transferred to a diagnostic instrument such as a blood testing device 60D.

Referring to FIGS. 7A-7D, in one embodiment, blood transfer device 10E includes a first end 150, a second end 152, an internal mechanism within the housing 14E of the blood transfer device 10E, and a cap 154 that is transitionable between an open position and a closed position.

During the use of blood transfer device 10E, a lancet device can be used to lance a skin surface S of a patient. Next, the cap 154 is removed to open the blood transfer device 10E and expose the material 16E within the blood transfer device 10E. The blood transfer device 10E is then positioned such that the material 16E is placed adjacent a punctured skin surface S of a patient so that the blood sample 12 can be transferred to the material 16E. For example, the material 16E may touch the punctured skin surface S to soak up the blood sample 12. As the blood 12 is loaded into the material 16E, the blood 12 is exposed to the anticoagulant powder throughout the internal micro pore structure of the material 16E. Once the material 16E is loaded with the blood 12, the cap 154 is connected to the blood transfer device 10E to close the blood transfer device 10E and the material 16E is deformed, e.g., compressed, to squeeze out a stabilized blood sample 12. For example, the blood transfer device 10E can be pushed down on a surface to trigger the internal mechanism within the housing 14E of the blood transfer device 10E to automatically compress the material 16E and squeeze a stabilized blood sample 12 through the dispensing tip 26E. In one embodiment, the stabilized blood sample 12 may be transferred to a diagnostic instrument such as a blood testing device 60E.

Figure 8:
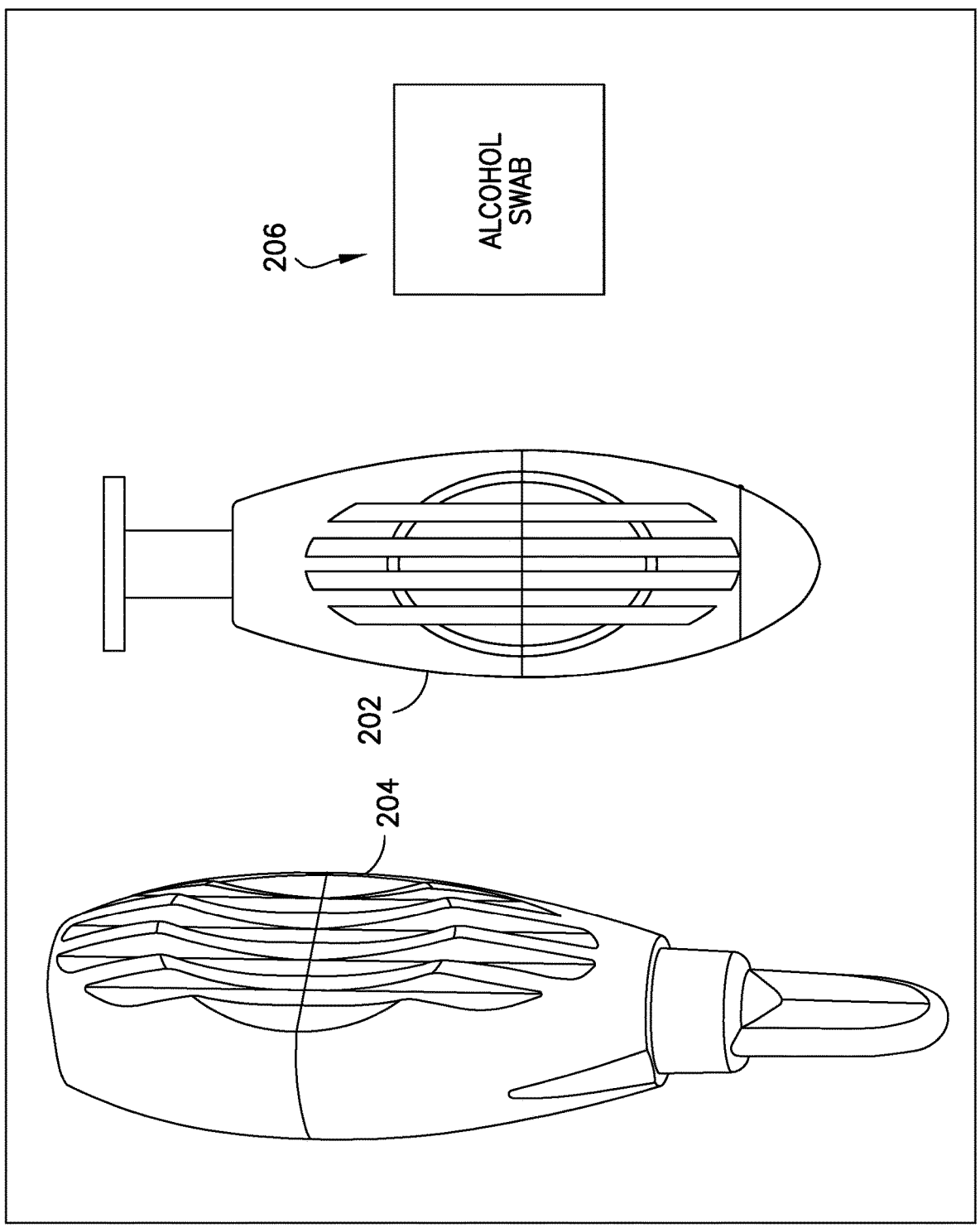
FIG. 8 is a top view of a blood transfer device kit in accordance with an embodiment of the present invention.
Figure 9:
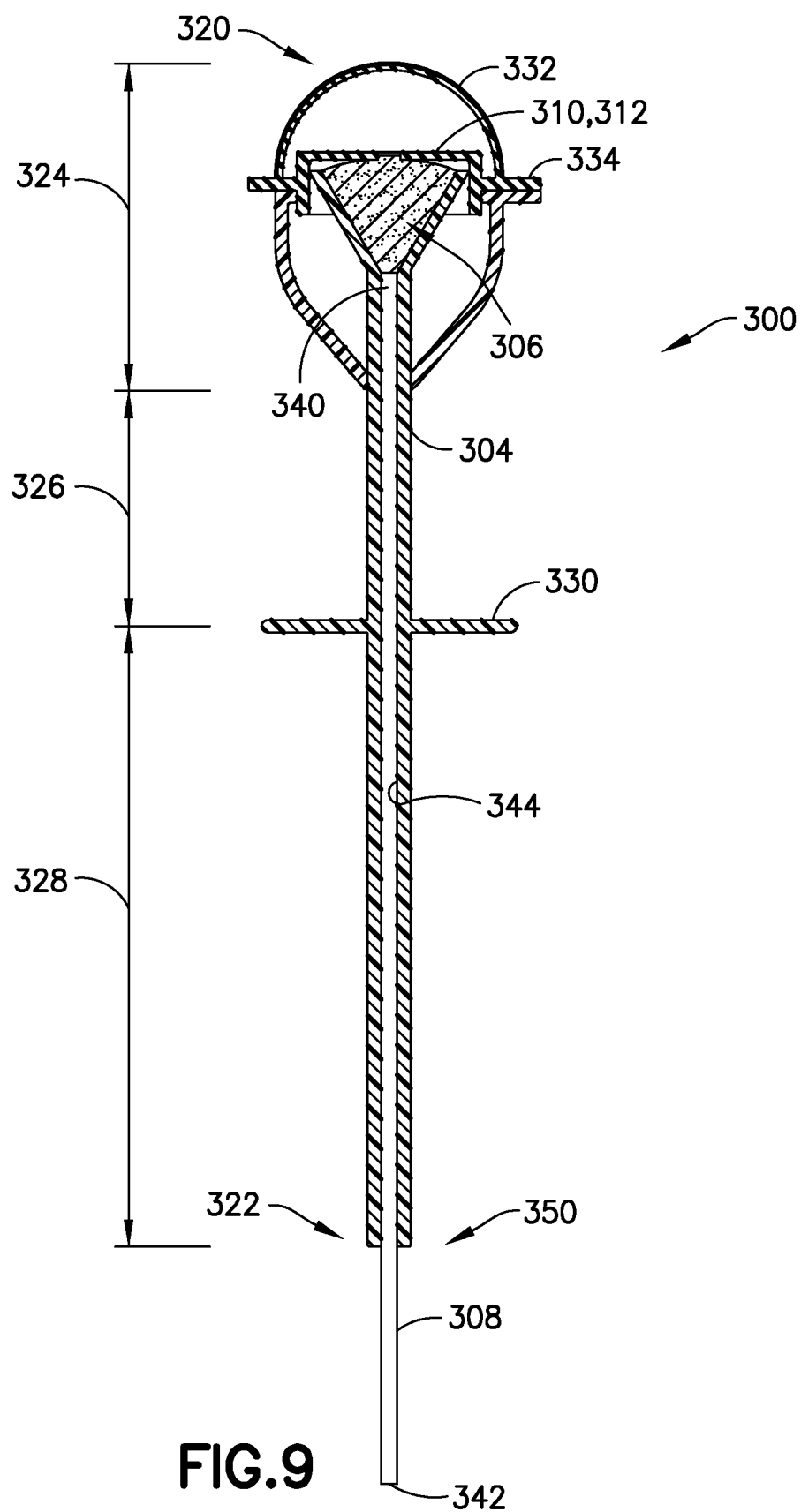
FIG. 9 is a cross-sectional front view of a blood transfer device in accordance with an embodiment of the present invention.

FIG. 8 illustrates an exemplary embodiment of the present disclosure. Referring to FIG. 8, a lancet and blood transfer system 200 of the present disclosure includes a kit 201 having a blood transfer device 202, a contact activated lancet device 204, and alcohol swabs 206. In one embodiment, the components of the kit 201 are packaged together.

Referring to FIGS. 1A-1E, operating principles of embodiments of the present disclosure are illustrated. Referring to FIGS. 1B and 1C, a deformable material 16 receives blood 12 therein. As the blood 12 is loaded into the material 16, the blood 12 is exposed to the anticoagulant powder throughout the internal micro pore structure of the material 16. Once the material 16 is loaded with the blood 12, the material 16 is directly deformed, e.g., compressed, to squeeze out a stabilized blood sample 12.

Referring to FIGS. 1D and 1E, a deformable material 16 receives blood 12 therein. As the blood 12 is loaded into the material 16, the blood 12 is exposed to the anticoagulant powder throughout the internal micro pore structure of the material 16. Once the material 16 is loaded with the blood 12, the material 16 is indirectly deformed, e.g., compressed, via the viscoelastic member 18 to squeeze out a stabilized blood sample 12.

A blood transfer device of the present disclosure offers uniform blood mixing with an anticoagulant throughout micro pores of an open cell foam for small sample volumes such as capillary blood samples obtained from a finger stick. A blood transfer device of the present disclosure could catch blood clots or other contaminants within the pores of the open cell foam and prevent them from being dispensed into a diagnostic sample port. A blood transfer device of the present disclosure enables a simple, low cost design for receiving and dispensing a blood sample. Blood sample management based on a deformable open cell foam may be used and adjusted for capillary, venous, and arterial sample management.

FIGS. 9-20 illustrate other exemplary embodiments of the present disclosure. The present disclosure also provides a blood transfer device that includes an open cell foam material and a capillary tube to collect a blood sample, stabilize the blood sample, e.g., mix the blood sample with an anticoagulant, meter the blood sample, and dispense the stabilized blood sample to a diagnostic device. The present disclosure also provides an open cell foam material that may be placed within a syringe assembly for mixing and stabilizing blood. For example, an open cell foam material may be used with an arterial blood gas syringe. In this manner, stabilized blood is dispensed for blood gas analysis.

FIGS. 9-13 illustrate an exemplary embodiment of a blood transfer device of the present disclosure. Referring to FIGS. 9-13, a blood transfer device 300 adapted to receive a blood sample 302 includes a housing 304, an open cell foam material 306 having a dry anticoagulant powder 310 therein, and a capillary tube 308.

Referring to FIGS. 9-13, housing 304 includes a first end 320, a second end 322, a first portion 324, a second portion 326, a third portion 328, a finger grip 330 disposed between the second portion 326 and the third portion 328, an actuation member 332 transitionable between a first position and a second position, and a lid 334 movable between a closed position in which the open cell foam material 306 is sealed within the housing 304 and an open position in which a portion of the open cell foam material 306 is exposed. With the lid 334 in the open position and the open cell foam material 306 in contact with the blood sample 302, the blood sample 302 is absorbed within the open cell foam material 306 and mixed with the dry anticoagulant powder 310 therein. In one embodiment, the actuation member 332 is a push button formed of a rubber material.

In one embodiment, open cell foam material 306 includes pores 312 and is disposed within the housing 304 of the blood transfer device 300. Referring to FIGS. 9-13, in one embodiment, the open cell foam material 306 is disposed within the first portion 324 of the housing 304. In one embodiment, the open cell foam material 306 includes a dry anticoagulant powder 310 within the pores 312 of the open cell foam material 306.

The open cell foam material 306 is adapted to receive a blood sample 302 such that the blood sample 302 is mixed with the dry anticoagulant powder 310 which is present inside the open cell foam material 306. In this manner, a stabilized blood sample may travel from the open cell foam material 306 into capillary tube 308 for final metering and dispensing as described in more detail below.

In one embodiment, the open cell foam 306 is treated with an anticoagulant to form a dry anticoagulant powder 310 finely distributed throughout the pores 312 of the open cell foam 306. The open cell foam 306 may be loaded with a blood sample 302. The blood 302 gets soaked into the open cell foam 306 based on capillary principles. As the blood 302 is loaded into the open cell foam 306, the blood 302 is exposed to the anticoagulant powder 310 throughout the internal micro pore structure of the open cell foam 306. The stabilized blood sample 302 may be transferred to a diagnostic instrument such as a blood testing device, a point-of-care testing device, or similar analytical device.

As described above, a method of loading an anticoagulant to the open cell foam material 306 having pores 312 may include soaking the open cell foam material 306 in a liquid solution of the anticoagulant and water; evaporating the water of the liquid solution; and forming a dry anticoagulant powder 310 within the pores 312 of the open cell foam material 306.

The method of the present disclosure enables precisely controlled loading of an anticoagulant into the open cell foam material 306 by soaking it with an anticoagulant and water solution and then drying the open cell foam material 306 to form a finely distributed dry anticoagulant powder 310 throughout the pores 312 of the open cell foam material 306.

Anticoagulants such as Heparin or EDTA (Ethylene Diamine Tetra Acetic Acid) as well as other blood stabilization agents could be introduced into the open cell foam material 306 as a liquid solution by soaking the open cell foam material 306 in the liquid solution of a desired concentration. After evaporating the liquid phase, e.g., evaporating the water from a water and Heparin solution, a dry anticoagulant powder may be formed and finely distributed throughout the internal structure of the open cell foam material 306. For example, the dry anticoagulant powder may be finely distributed throughout the pores 312 of the open cell foam material 306. In a similar manner, the open cell foam material 306 could be treated to provide a hydrophobic, hydrophilic, or reactive internal pore surface.

Referring to FIGS. 9-13, capillary tube 308 is in fluid communication with the open cell foam material 306 and a portion of the capillary tube 308 is disposed within the housing 304 of the blood transfer device 300. The capillary tube 308 includes a first end 340, a dispensing tip 342, and an internal wall surface 344. The first end 340 of the capillary tube 308 is in fluid communication with the open cell foam material 306. In one embodiment, the internal wall surface 344 of the capillary tube 308 includes an anticoagulant coating.

Figure 13:
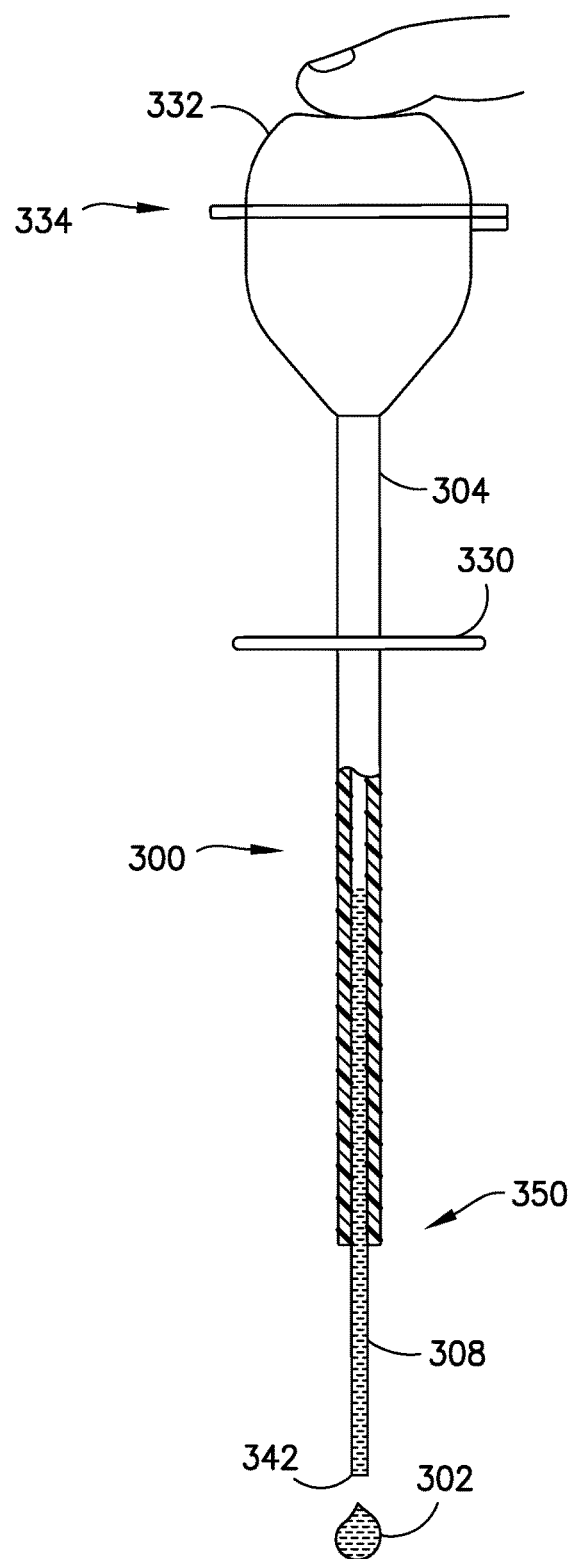
FIG. 13 is a front view of a step of using the blood transfer device of FIG. 9 in accordance with an embodiment of the present invention.
Figure 14:
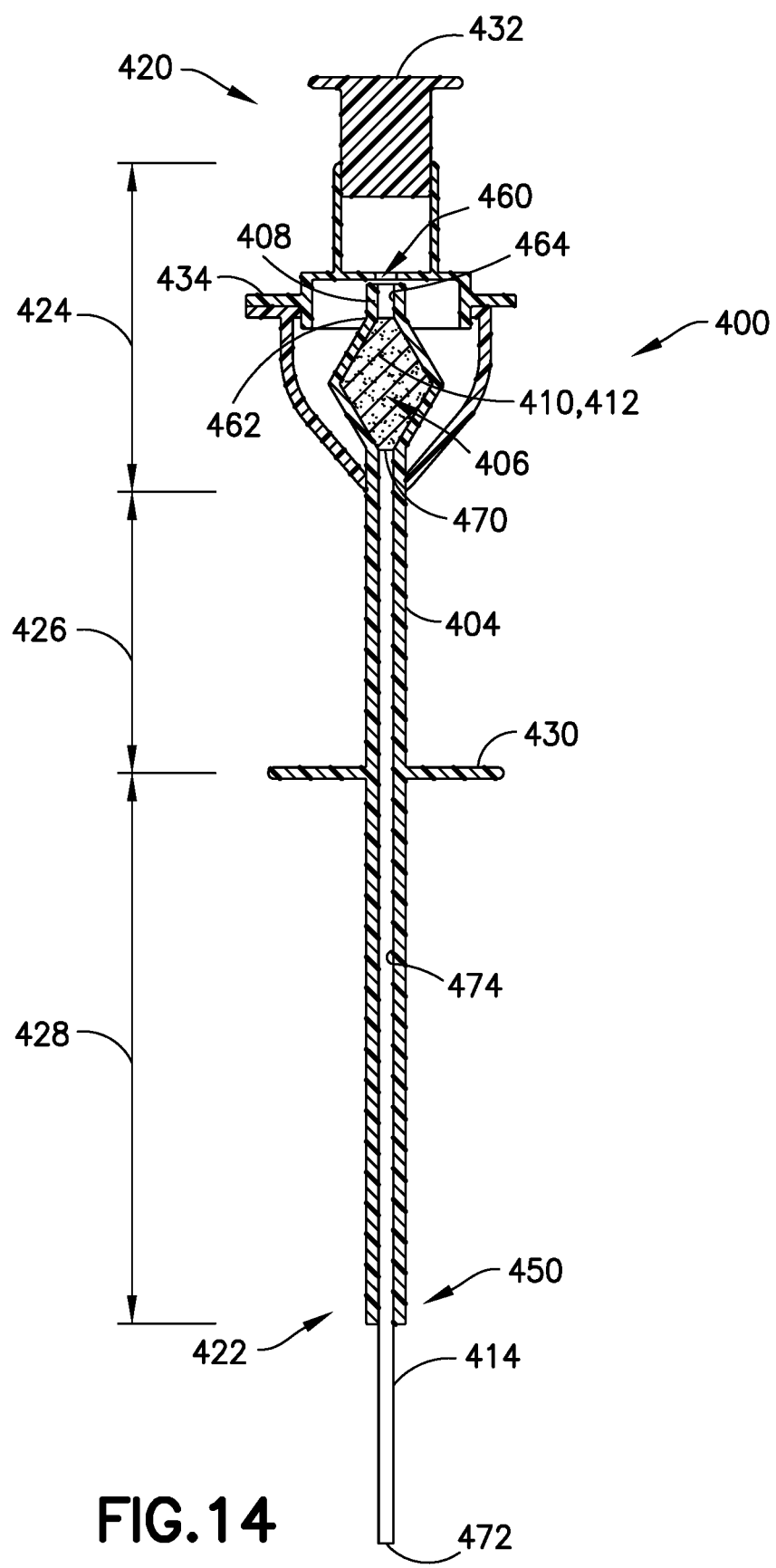
FIG. 14 is a cross-sectional front view of a blood transfer device in accordance with an embodiment of the present invention.

The capillary tube 308 is adapted to receive the blood sample 302 after the blood sample 302 is mixed with the dry anticoagulant powder 310 within the open cell foam material 306. Referring to FIG. 13, with the blood sample 302 received within the capillary tube 308, movement of the actuation member 332 from the first position to the second position dispenses the blood sample 302 through the dispensing tip 342 of the capillary tube 308.

In one embodiment, the capillary tube 308 or the housing 304 of the blood transfer device 300 may include fill lines, such as graduations located on a sidewall 350 of blood transfer device 300, for providing an indication as to the level or amount of stabilized blood sample 302 contained within capillary tube 308. Such markings may be provided on an external surface of sidewall 350, an internal surface of sidewall 350, or integrally formed or otherwise within sidewall 350 of blood transfer device 300.

Referring to FIGS. 10-13, during the use of blood transfer device 300 to collect a blood sample 302, stabilize the blood sample 302, e.g., mix the blood sample 302 with an anticoagulant, meter the blood sample 302, and dispense the stabilized blood sample 302 to a diagnostic device, a lancet device can be used to lance a skin surface S of a patient.

Figure 10:
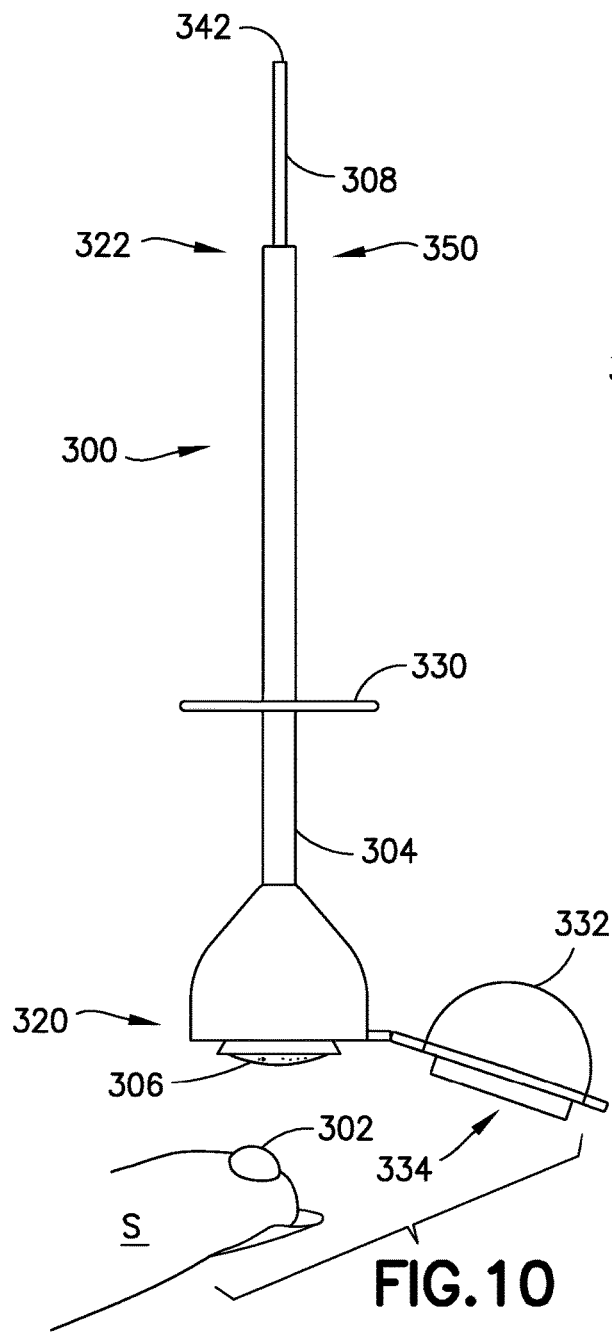
FIG. 10 is a front view of a step of using the blood transfer device of FIG. 9 in accordance with an embodiment of the present invention.

Next, referring to FIG. 10, the lid 334 is moved to the open position to expose a portion of the open cell foam material 306. The blood transfer device 300 is then positioned such that the open cell foam material 306 is placed adjacent a punctured skin surface S of a patient so that the blood sample 302 can be transferred to the open cell foam material 306. For example, when a drop of blood 302 comes in contact with the open cell foam material 306, the blood 302 is instantly absorbed due to a strong capillary action of multiple open cell foam pores 312.

Figure 11:
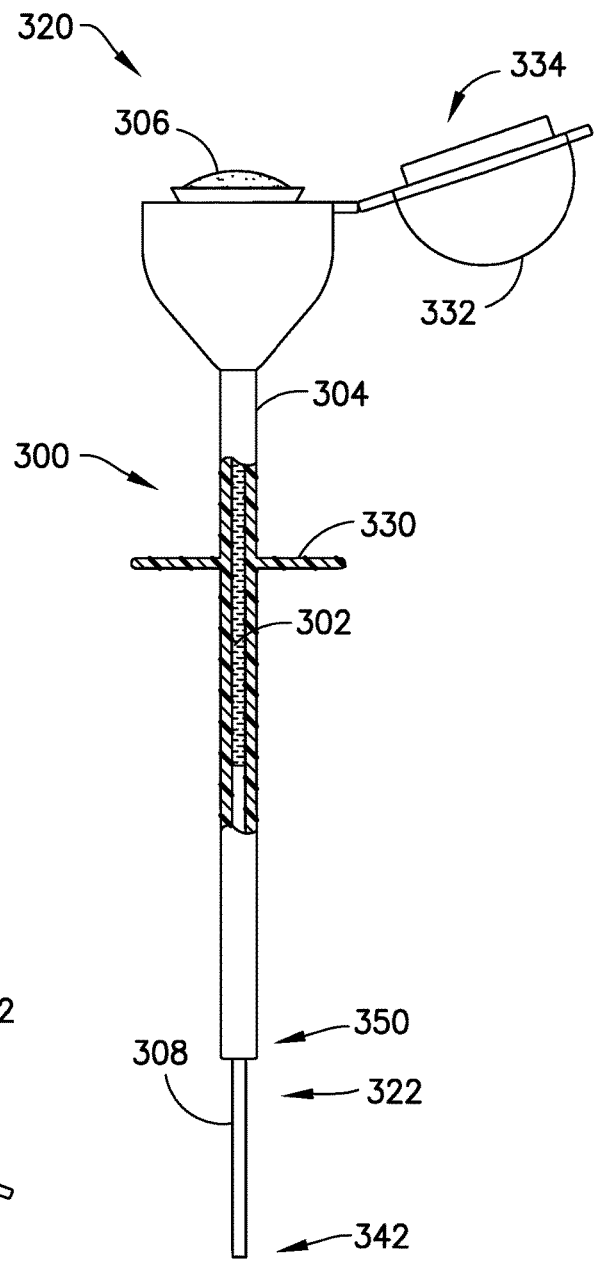
FIG. 11 is a front view of a step of using the blood transfer device of FIG. 9 in accordance with an embodiment of the present invention.
Figure 12:
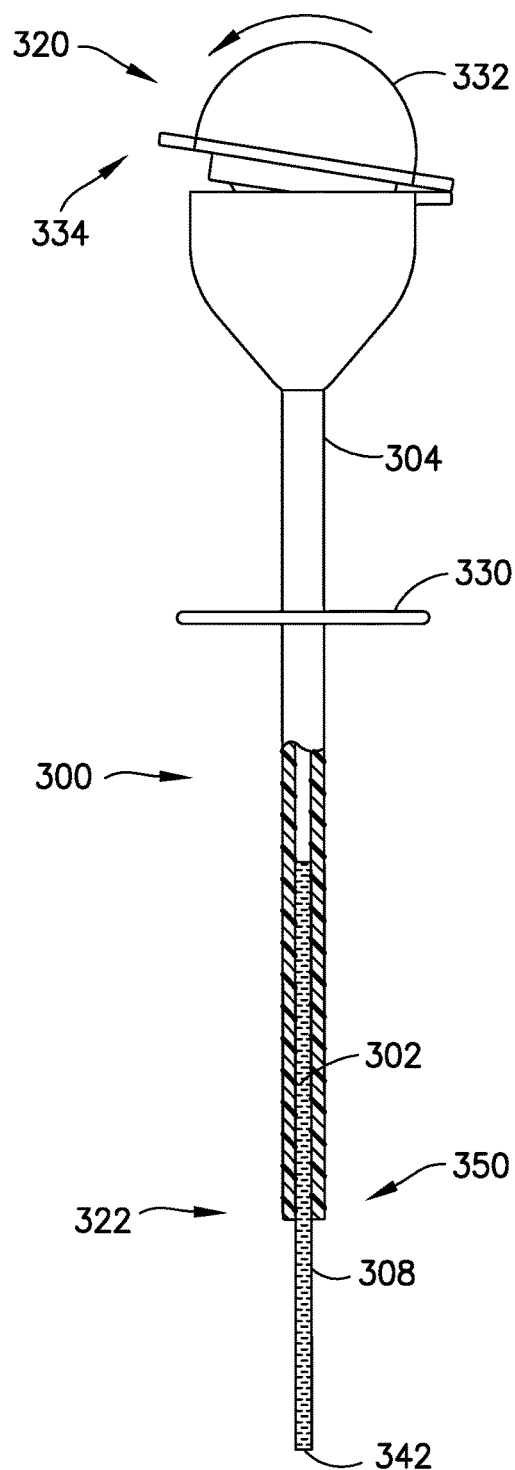
FIG. 12 is a front view of a step of using the blood transfer device of FIG. 9 in accordance with an embodiment of the present invention.

As the blood 302 is loaded into the open cell foam material 306, the blood 302 is exposed to the anticoagulant powder 310 throughout the internal micro pore structure of the open cell foam material 306. Referring to FIGS. 11 and 12, once the open cell foam material 306 is loaded with the blood 302, the lid 334 is moved to the closed position in which the open cell foam material 306 is sealed within the housing 304 and the stabilized blood sample 302 is drawn from the open cell foam material 306 into the capillary tube 308.

Referring to FIG. 11, with the second end 322 of the blood transfer device 300 positioned below the first end 320, the capillary blood transfer from the open cell foam material 306 to the capillary tube 308 is improved. In one embodiment, the internal wall surface 344 of the capillary tube 308 includes an anticoagulant coating to provide a second stage of mixing for the stabilized blood sample 302.

The stabilized blood sample 302 is allowed to fill up the capillary tube 308 to the appropriate marking or fill line, such as the graduations located on a sidewall 350 of blood transfer device 300 as described above. In one embodiment, the length of the capillary tube 308 up to a marking defines the volume of the blood sample collected, e.g., blood metering.

Referring to FIG. 13, movement of the actuation member 332 from the first position to the second position dispenses the stabilized blood sample 302 through the dispensing tip 342 of the capillary tube 308. For example, the stabilized blood sample 302 may be dispensed from the capillary tube 308 using air pressure. In one embodiment, the actuation member 332 is a push button that can be pushed to dispense the stabilized blood sample 302. For example, when it is desired to expel the stabilized blood sample 302 contained within capillary tube 308, the blood transfer device 300 may be grasped with the user's thumb on actuation member 332 of housing 304 and with the user's fingers extending around finger grip 330. Next, the user effects a squeezing movement between the thumb on actuation member 332 of housing 304 and four fingers grasping finger grip 330, thereby causing actuation member 332 to be pushed or moved from the first position to the second position. In one embodiment, the stabilized blood sample 302 may be transferred to a diagnostic instrument such as a blood testing device.

The blood transfer device 300 includes an open cell foam material 306 and a capillary tube 308 to collect a blood sample 302, stabilize the blood sample 302, e.g., mix the blood sample 302 with a dry anticoagulant powder 310 within the open cell foam material 306, meter the blood sample 302, and dispense the stabilized blood sample to a diagnostic device.

Capillary blood samples may be transferred by capillary tubes that have an internal wall coated with a dry anticoagulant. Such capillary tubes might result in insufficient blood mixing with the anticoagulant due to the laminar nature of the capillary flow and slow diffusion kinetics of the dry anticoagulant. The blood transfer device 300 of the present disclosure enables more uniform mixing of a capillary blood sample by mixing the blood sample with a dry anticoagulant powder 310 within the open cell foam material 306 before it enters the capillary tube 308 for final dispensing.

FIGS. 14-18 illustrate another exemplary embodiment of a blood transfer device of the present disclosure. Referring to FIGS. 14-18, a blood transfer device 400 adapted to receive a blood sample 402 includes a housing 404, an open cell foam material 406 having a dry anticoagulant powder 410 therein, a first capillary tube 408, and a second capillary tube 414.

Referring to FIGS. 14-18, housing 404 includes a first end 420, a second end 422, a first portion 424, a second portion 426, a third portion 428, a finger grip 430 disposed between the second portion 426 and the third portion 428, an actuation member 432 transitionable between a first position and a second position, and a lid 434 movable between a closed position in which an inlet 460 of the first capillary tube 408 and the open cell foam material 406 are sealed within the housing 404 and an open position in which the inlet 460 of the first capillary tube 408 is exposed. With the lid 434 in the open position and the inlet 460 of the first capillary tube 408 in contact with the blood sample 402, the blood sample 402 is transferred to the open cell foam material 406 via the first capillary tube 408 and mixed with the dry anticoagulant powder 410 therein. In one embodiment, the actuation member 432 is a plunger.

In one embodiment, open cell foam material 406 includes pores 412 and is disposed within the housing 404 of the blood transfer device 400. Referring to FIGS. 14-18, in one embodiment, the open cell foam material 406 is disposed within the first portion 424 of the housing 404. In one embodiment, the open cell foam material 406 includes a dry anticoagulant powder 410 within the pores 412 of the open cell foam material 406.

As described above, the open cell foam material 406 is adapted to receive a blood sample 402 such that the blood sample 402 is mixed with the dry anticoagulant powder 410 which is present inside the open cell foam material 406. In this manner, a stabilized blood sample may travel from the open cell foam material 406 into the second capillary tube 414 for final metering and dispensing as described in more detail below.

In one embodiment, the open cell foam 406 is treated with an anticoagulant to form a dry anticoagulant powder 410 finely distributed throughout the pores 412 of the open cell foam 406. The open cell foam 406 may be loaded with a blood sample 402. The blood sample 402 is transferred to the open cell foam material 406 via the first capillary tube 408. As the blood 402 is loaded into the open cell foam 406, the blood 402 is exposed to the anticoagulant powder 410 throughout the internal micro pore structure of the open cell foam 406. The stabilized blood sample 402 may be transferred to a diagnostic instrument such as a blood testing device, a point-of-care testing device, or similar analytical device.

In one embodiment, the open cell foam material 406 is a soft deformable open cell foam that is inert to blood. In one embodiment, the open cell foam material 406 is a Basotect® foam available from BASF. Such a foam is a Melamine foam which is an open cell foam material consisting of a formaldehyde-melamine-sodium bisulfite copolymer. The Melamine foam is a flexible, hydrophilic open cell foam that is resistant to heat and many organic solvents. In one embodiment, the open cell foam material 406 may be a sponge material.

As described above, a method of loading an anticoagulant to the open cell foam material 406 having pores 412 may include soaking the open cell foam material 406 in a liquid solution of the anticoagulant and water; evaporating the water of the liquid solution; and forming a dry anticoagulant powder 410 within the pores 412 of the open cell foam material 406.

The method of the present disclosure enables precisely controlled loading of an anticoagulant into the open cell foam material 406 by soaking it with an anticoagulant and water solution and then drying the open cell foam material 406 to form a finely distributed dry anticoagulant powder 410 throughout the pores 412 of the open cell foam material 406.

Anticoagulants such as Heparin or EDTA (Ethylene Diamine Tetra Acetic Acid) as well as other blood stabilization agents could be introduced into the open cell foam material 406 as a liquid solution by soaking the open cell foam material 406 in the liquid solution of a desired concentration. After evaporating the liquid phase, e.g., evaporating the water from a water and Heparin solution, a dry anticoagulant powder may be formed and finely distributed throughout the internal structure of the open cell foam material 406. For example, the dry anticoagulant powder may be finely distributed throughout the pores 412 of the open cell foam material 406. In a similar manner, the open cell foam material 406 could be treated to provide a hydrophobic, hydrophilic, or reactive internal pore surface.

Referring to FIGS. 14-18, the blood transfer device 400 includes a first capillary tube 408 and a second capillary tube 414. The first capillary tube 408 is in fluid communication with the open cell foam material 406 and is disposed between the first end 420 of the housing 404 and the open cell foam material 406. The second capillary tube 414 is in fluid communication with the open cell foam material 406 and is disposed between the second end 422 of the housing 404 and the open cell foam material 406. Thus, the open cell foam material 406 is disposed between the first capillary tube 408 and the second capillary tube 414. In this manner, referring to FIG. 14, the housing 404, the first capillary tube 408, and the second capillary tube 414 protects the open cell foam material 406 within the blood transfer device 400.

The first capillary tube 408 includes an inlet 460, a second end 462, and an internal wall surface 464. The first capillary tube 408 is in fluid communication with the open cell foam material 406 and a portion of the first capillary tube 408 is disposed within the housing 404 of the blood transfer device 400. The second end 462 of the first capillary tube 408 is in fluid communication with the open cell foam material 406. In one embodiment, the internal wall surface 464 of the first capillary tube 408 includes an anticoagulant coating.

Referring to FIG. 15, with the lid 434 of housing 404 in the open position and the inlet 460 of the first capillary tube 408 in contact with the blood sample 402, the blood sample 402 is transferred to the open cell foam material 406 via the first capillary tube 408 and mixed with the dry anticoagulant powder 410 therein.

The second capillary tube 414 includes a first end 470, a dispensing tip 472, and an internal wall surface 474. The second capillary tube 414 is in fluid communication with the open cell foam material 406 and a portion of the second capillary tube 414 is disposed within the housing 404 of the blood transfer device 400. The first end 470 of the second capillary tube 414 is in fluid communication with the open cell foam material 406. In one embodiment, the internal wall surface 474 of the second capillary tube 414 includes an anticoagulant coating.

The second capillary tube 414 is adapted to receive the blood sample 402 after the blood sample 402 is mixed with the dry anticoagulant powder 410 within the open cell foam material 406. Referring to FIG. 18, with the blood sample 402 received within the second capillary tube 414, movement of the actuation member 432 from the first position to the second position dispenses the blood sample 402 through the dispensing tip 472 of the second capillary tube 414.

In one embodiment, the second capillary tube 414 or the housing 404 of the blood transfer device 400 may include fill lines, such as graduations located on a sidewall 450 of blood transfer device 400, for providing an indication as to the level or amount of stabilized blood sample 402 contained within second capillary tube 414. Such markings may be provided on an external surface of sidewall 450, an internal surface of sidewall 450, or integrally formed or otherwise within sidewall 450 of blood transfer device 400.

Referring to FIGS. 14-18, in one embodiment, the first capillary tube 408 and the second capillary tube 414 have different lengths. For example, in one embodiment, the first capillary tube 408 may be shorter than the second capillary tube 414. In one embodiment, the first capillary tube 408 and the second capillary tube 414 have different internal diameters.

Referring to FIGS. 15-18, during the use of blood transfer device 400 to collect a blood sample 402, stabilize the blood sample 402, e.g., mix the blood sample 402 with an anticoagulant, meter the blood sample 402, and dispense the stabilized blood sample 402 to a diagnostic device, a lancet device can be used to lance a skin surface S of a patient.

Next, referring to FIG. 15, the lid 434 is moved to the open position to expose the inlet 460 of the first capillary tube 408. The blood transfer device 400 is then positioned such that the inlet 460 of the first capillary tube 408 is placed adjacent a punctured skin surface S of a patient so that the blood sample 402 can be transferred to the open cell foam material 406 via the first capillary tube 408.

As the blood 402 is loaded into the open cell foam material 406 via the first capillary tube 408, the blood 402 is exposed to the anticoagulant powder 410 throughout the internal micro pore structure of the open cell foam material 406. Referring to FIGS. 16 and 17, once the open cell foam material 406 is loaded with the blood 402, the lid 434 is moved to the closed position in which the inlet 460 of the first capillary tube 408 and the open cell foam material 406 are sealed within the housing 404 and the stabilized blood sample 402 is drawn from the open cell foam material 406 into the second capillary tube 414.

Referring to FIG. 16, with the second end 422 of the blood transfer device 400 positioned below the first end 420, the capillary blood transfer from the open cell foam material 406 to the second capillary tube 414 is improved. In one embodiment, the internal wall surface 474 of the second capillary tube 414 includes an anticoagulant coating to provide a second stage of mixing for the stabilized blood sample 402.

The stabilized blood sample 402 is allowed to fill up the second capillary tube 414 to the appropriate marking or fill line, such as the graduations located on a sidewall 450 of blood transfer device 400 as described above. In one embodiment, the length of the second capillary tube 414 up to a marking defines the volume of the blood sample collected, e.g., blood metering.

Referring to FIG. 18, movement of the actuation member 432 from the first position to the second position dispenses the stabilized blood sample 402 through the dispensing tip 472 of the second capillary tube 414. For example, the stabilized blood sample 402 may be dispensed from the second capillary tube 414 using air pressure. In one embodiment, the actuation member 432 is a plunger that can be pushed to dispense the stabilized blood sample 402. For example, when it is desired to expel the stabilized blood sample 402 contained within second capillary tube 414, the blood transfer device 400 may be grasped with the user's thumb on actuation member 432 of housing 404 and with the user's fingers extending around finger grip 430. Next, the user effects a squeezing movement between the thumb on actuation member 432 of housing 404 and four fingers grasping finger grip 430, thereby causing actuation member 432 to be pushed or moved from the first position to the second position. In one embodiment, the stabilized blood sample 402 may be transferred to a diagnostic instrument such as a blood testing device.

The blood transfer device 400 includes an open cell foam material 406 and a first capillary tube 408 and second capillary tube 414 to collect a blood sample 402, stabilize the blood sample 402, e.g., mix the blood sample 402 with a dry anticoagulant powder 410 within the open cell foam material 406, meter the blood sample 402, and dispense the stabilized blood sample to a diagnostic device.

Capillary blood samples may be transferred by capillary tubes that have an internal wall coated with a dry anticoagulant. Such capillary tubes might result in insufficient blood mixing with the anticoagulant due to the laminar nature of the capillary flow and slow diffusion kinetics of the dry anticoagulant. The blood transfer device 400 of the present disclosure enables more uniform mixing of a capillary blood sample by mixing the blood sample with a dry anticoagulant powder 410 within the open cell foam material 406 before it enters the second capillary tube 414 for final dispensing.

FIGS. 19 and 20 illustrate an exemplary embodiment of a syringe assembly of the present disclosure. Referring to FIGS. 19 and 20, a syringe assembly 500 includes an open cell foam material 502 having a dry anticoagulant powder 504 therein. The open cell foam material 502 is disposed within the syringe assembly 500.

In one embodiment, the syringe assembly 500 includes a syringe barrel 506 having a first end 508, a second end 510, and a sidewall 512 extending therebetween and defining an interior 514. Referring to FIGS. 19 and 20, the open cell foam material 502 is disposed within the interior 514 of the syringe barrel 506.

In one embodiment, the syringe assembly 500 includes a plunger rod 516 and a stopper 518. The plunger rod 516 includes a first end and a second end. The stopper 518 is engaged with the second end 522 of the plunger rod 516 and is slidably disposed within the interior 514 of the syringe barrel 506. The stopper 518 is sized relative to the interior 514 of the syringe barrel 506 to provide sealing engagement with the sidewall 512 of the syringe barrel 506.

The open cell foam material 502 is placed in the syringe barrel 506 for mixing and stabilizing blood. The blood gets collected in the syringe barrel 506 with the open cell foam material 502 embedded inside the syringe barrel 506. The stabilized blood can then be dispensed for analysis. In one embodiment, the syringe assembly is an arterial blood gas syringe and the stabilized blood can be dispensed for blood gas analysis.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A blood transfer device adapted to receive a blood sample, comprising:

a housing having a blood inlet port, a blood outlet port separate from the blood inlet port, and an actuation member provided adjacent the blood inlet port of the housing and transitionable between a first position and a second position; and an open cell foam material disposed within the housing and having a dry anticoagulant powder therein, wherein the actuation member is adapted to cover the open cell foam material at the blood inlet port, wherein the housing further comprises a lid movable between a closed position in which the open cell foam material is sealed within the housing and the actuation member covers the open cell foam material at the blood inlet port and an open position in which a portion of the open cell foam material is exposed beyond the blood inlet port.

2. The blood transfer device of claim 1, further comprising a capillary tube in fluid communication with the open cell foam material.

3. The blood transfer device of claim 2, wherein the capillary tube is adapted to receive the blood sample after the blood sample is mixed with the dry anticoagulant powder within the open cell foam material.

4. The blood transfer device of claim 2, wherein the capillary tube includes a dispensing tip provided at the blood outlet port.

5. The blood transfer device of claim 4, wherein movement of the actuation member from the first position to the second position dispenses the blood sample through the dispensing tip of the capillary tube.

6. A blood transfer device adapted to receive a blood sample, comprising:

a housing having a blood inlet port, a blood outlet port separate from the blood inlet port, and an actuation member provided adjacent the blood inlet port of the housing and transitionable between a first position and a second position;

an open cell foam material disposed within the housing and having a dry anticoagulant powder therein;

a first capillary tube in fluid communication with the open cell foam material, wherein the actuation member is adapted to cover the open cell foam material at the blood inlet port, wherein the first capillary tube is disposed between the blood inlet port of the housing and the open cell foam material; and a second capillary tube in fluid communication with the open cell foam material, the second capillary tube disposed between the blood outlet port of the housing and the open cell foam material.

7. The blood transfer device of claim 6, wherein the second capillary tube is adapted to receive the blood sample after the blood sample is mixed with the dry anticoagulant powder within the open cell foam material.

8. The blood transfer device of claim 6, wherein movement of the actuation member from the first position to the second position dispenses the blood sample through a dispensing tip of the second capillary tube.

9. The blood transfer device of claim 6, wherein at least one of an internal surface of the first capillary tube and an internal surface of the second capillary tube includes an anticoagulant coating.

10. The blood transfer device of claim 6, wherein the first capillary tube and the second capillary tube have different lengths.

11. The blood transfer device of claim 6, wherein the first capillary tube and the second capillary tube have different internal diameters.

12. The blood transfer device of claim 1, wherein the actuation member is adapted to encapsulate the open cell foam material within the housing.

13. The blood transfer device of claim 1, wherein, when the actuation member transitions between the first position and the second position, the actuation member rotates about an axis.

14. The blood transfer device of claim 1, wherein, when the actuation member transitions from the first position to the second position, at least a portion of the actuation member moves away from the open cell foam material.

* * * * *